# (12) United States Patent
Feldhaus

(10) Patent No.: US 6,936,466 B2
(45) Date of Patent: *Aug. 30, 2005

(54) TRANSCRIPTIONALLY-ACTIVATED AAV INVERTED TERMINAL REPEATS (ITRS) FOR USE WITH RECOMBINANT AAV VECTORS

(75) Inventor: Andrew L. Feldhaus, Lynnwood, WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/909,363

(22) Filed: Jul. 19, 2001

(65) Prior Publication Data

US 2002/0164783 A1 Nov. 7, 2002

Related U.S. Application Data

(63) Continuation of application No. 09/171,759, filed as application No. PCT/US98/21937 on Oct. 20, 1998, now Pat. No. 6,346,415.
(60) Provisional application No. 60/108,162, filed on Oct. 21, 1997.

(51) Int. Cl.$^7$ .......................... C12N 15/84; C12N 7/01; C12N 5/10
(52) U.S. Cl. ................ 435/320.1; 435/325; 435/235.1; 435/440; 435/455; 435/456; 435/457; 536/23.72; 536/24.1; 536/23.5
(58) Field of Search .............................. 435/320.1, 325, 435/235.1, 440, 455–457; 536/23.72, 24.1, 23.5

(56) References Cited

U.S. PATENT DOCUMENTS

| | | |
|---|---|---|
| 4,797,368 A | 1/1989 | Carter et al. |
| 5,139,941 A | 8/1992 | Muzyczka et al. |
| 5,252,479 A | 10/1993 | Srivastava |
| 5,387,484 A | 2/1995 | Doany et al. |
| 5,587,308 A | 12/1996 | Carter et al. |
| 5,587,508 A | 12/1996 | Machida |
| 5,652,224 A | 7/1997 | Wilson et al. |
| 5,658,776 A | 8/1997 | Flotte et al. |
| 5,658,785 A | 8/1997 | Johnson |
| 5,731,182 A | 3/1998 | Boyce |
| 5,756,283 A | 5/1998 | Wilson et al. |
| 5,786,211 A | 7/1998 | Johnson |
| 5,837,484 A | 11/1998 | Trempe et al. |
| 5,856,152 A | 1/1999 | Wilson et al. |
| 5,858,775 A | 1/1999 | Johnson |
| 5,866,552 A | 2/1999 | Wilson et al. |
| 5,866,696 A | 2/1999 | Carter et al. |
| 5,871,982 A | 2/1999 | Wilson et al. |
| 5,871,986 A | 2/1999 | Boyce |
| 5,872,154 A | 2/1999 | Wilson et al. |
| 5,989,540 A | 11/1999 | Carter et al. |
| 5,990,279 A | 11/1999 | Carter et al. |
| 6,001,557 A | 12/1999 | Wilson et al. |
| 6,165,781 A | 12/2000 | Carter et al. |
| 6,174,527 B1 | 1/2001 | Wilson et al. |
| 6,183,993 B1 | 2/2001 | Boyce et al. |
| 6,187,532 B1 | 2/2001 | Wood et al. |
| 6,190,887 B1 | 2/2001 | Boyce et al. |
| 6,197,527 B1 | 3/2001 | Lynch et al. |
| 6,203,975 B1 | 3/2001 | Wilson et al. |
| 6,211,160 B1 | 4/2001 | Wilson et al. |
| 6,238,914 B1 | 5/2001 | Boyce |
| 6,251,677 B1 | 6/2001 | Wilson et al. |
| 6,251,957 B1 | 6/2001 | Wilson et al. |
| 6,258,595 B1 | 7/2001 | Gao et al. |
| 6,261,551 B1 | 7/2001 | Wilson et al. |
| 6,270,996 B1 | 8/2001 | Wilson et al. |
| 6,274,354 B1 | 8/2001 | Wilson et al. |
| 6,281,009 B1 | 8/2001 | Boyce |
| 6,281,010 B1 | 8/2001 | Gao et al. |
| 6,338,953 B1 | 1/2002 | Boyce et al. |
| 6,338,962 B1 | 1/2002 | Boyce |
| 6,346,415 B1 * | 2/2002 | Feldhaus .................. 435/320.1 |
| 6,372,208 B1 | 4/2002 | Wilson et al. |
| 6,387,368 B1 | 5/2002 | Wilson et al. |
| 6,399,370 B1 | 6/2002 | Wilson et al. |
| 6,399,385 B1 | 6/2002 | Croyle et al. |
| 6,428,988 B1 | 8/2002 | Wilson et al. |
| 6,436,392 B1 | 8/2002 | Engelhardt et al. |
| 6,475,769 B1 | 11/2002 | Wilson et al. |
| 6,482,634 B1 | 11/2002 | Wilson et al. |
| 6,485,966 B2 | 11/2002 | Gao et al. |
| 6,537,540 B1 | 3/2003 | Burstein et al. |
| 6,541,258 B2 | 4/2003 | Allen et al. |
| 6,548,286 B1 | 4/2003 | Samulski et al. |
| 6,566,118 B1 | 5/2003 | Atkinson et al. |
| 6,596,535 B1 | 7/2003 | Carter |
| 6,610,290 B2 | 8/2003 | Podsakoff et al. |
| 6,632,670 B1 | 10/2003 | Wadsworth et al. |

(Continued)

FOREIGN PATENT DOCUMENTS

| | | |
|---|---|---|
| WO | WO 93/24641 A2 | 12/1993 |
| WO | WO 93/24641 A3 | 12/1993 |
| WO | WO 95/13365 | 5/1995 |
| WO | WO 95/13392 A1 | 5/1995 |
| WO | WO 95/34670 | 12/1995 |

(Continued)

OTHER PUBLICATIONS

Aird, W.C. et al. (1995). "Human von Willebrand Factor Gene Sequences Target Expression to a Subpopulation of Endothelial Cells in Transgenic Mice," *PNAS* 92:4567–4571.

(Continued)

*Primary Examiner*—Mary E. Mosher
(74) *Attorney, Agent, or Firm*—Morrison & Foerster LLP

(57) ABSTRACT

This invention provides transcriptionally-activated AAV ITRs (inverted terminal repeats) which are small and transcriptionally active and uses thereof to optimize the expression of relatively large transgenes packaged in recombinant AAV vectors.

109 Claims, 2 Drawing Sheets"

U.S. PATENT DOCUMENTS

| | | |
|---|---|---|
| 6,642,051 B1 | 11/2003 | Lynch et al. |
| 6,759,237 B1 | 7/2004 | Wilson et al. |
| 2001/0006955 A1 | 7/2001 | Wilson et al. |
| 2002/0001581 A1 | 1/2002 | Lynch et al. |
| 2002/0032163 A1 | 3/2002 | Wilson et al. |
| 2002/0037867 A1 | 3/2002 | Wilson et al. |
| 2002/0081297 A1 | 6/2002 | Wilson et al. |
| 2002/0127582 A1 | 9/2002 | Atkinson et al. |
| 2002/0159979 A1 | 10/2002 | Johnson |
| 2002/0160501 A1 | 10/2002 | Atkinson et al. |
| 2002/0182182 A1 | 12/2002 | Wilson et al. |
| 2002/0197237 A1 | 12/2002 | Engelhardt et al. |
| 2003/0040101 A1 | 2/2003 | Wilosn et al. |
| 2003/0073232 A1 | 4/2003 | Wilson et al. |
| 2003/0082145 A1 | 5/2003 | Johnson |
| 2003/0103939 A1 | 6/2003 | Engelhardt et al. |
| 2003/0103942 A1 | 6/2003 | Burstein et al. |
| 2003/0113295 A1 | 6/2003 | Burstein et al. |
| 2003/0119191 A1 | 6/2003 | Gao et al. |
| 2003/0175974 A1 | 9/2003 | Allen |
| 2003/0219735 A1 | 11/2003 | Carter |
| 2004/0052764 A1 | 3/2004 | Hildinger et al. |
| 2004/0057931 A1 | 3/2004 | Wilson et al. |
| 2004/0057932 A1 | 3/2004 | Wilson et al. |
| 2004/0057933 A1 | 3/2004 | Wilson et al. |
| 2004/0062752 A1 | 4/2004 | Walsh et al. |

FOREIGN PATENT DOCUMENTS

| | | |
|---|---|---|
| WO | WO 96/09074 | 3/1996 |
| WO | WO 96/13597 | 5/1996 |
| WO | WO 96/13598 | 5/1996 |
| WO | WO 96/17947 A1 | 6/1996 |
| WO | WO 96/26285 | 8/1996 |
| WO | WO 96/26286 | 8/1996 |
| WO | WO 96/39530 | 12/1996 |
| WO | WO 97/32990 | 9/1997 |
| WO | WO 98/07833 | 2/1998 |
| WO | WO 98/09656 | 3/1998 |
| WO | WO 98/09657 | 3/1998 |
| WO | WO 98/10086 | 3/1998 |
| WO | WO 98/10088 | 3/1998 |
| WO | WO 98/11243 | 3/1998 |
| WO | WO 98/27204 A3 | 6/1998 |
| WO | WO 98/27204 A2 | 6/1998 |
| WO | WO 98/27207 A1 | 6/1998 |
| WO | WO 99/11764 A2 | 3/1999 |
| WO | WO 99/11764 A3 | 3/1999 |
| WO | WO 99/14351 | 3/1999 |
| WO | WO 99/15677 | 4/1999 |
| WO | WO 99/15685 | 4/1999 |
| WO | WO 99/20773 A3 | 4/1999 |
| WO | WO 99/20773 A2 | 4/1999 |
| WO | WO 99/20779 A1 | 4/1999 |
| WO | WO 99/47691 | 9/1999 |
| WO | WO 99/60146 | 11/1999 |
| WO | WO 00/14205 A2 | 3/2000 |
| WO | WO 00/14205 A3 | 3/2000 |
| WO | WO 00/28061 | 5/2000 |
| WO | WO 00/55342 | 9/2000 |
| WO | WO 00/65038 | 11/2000 |
| WO | WO 00/73480 | 12/2000 |
| WO | WO 00/73481 | 12/2000 |
| WO | WO 00/75353 | 12/2000 |
| WO | WO 00/75365 | 12/2000 |
| WO | WO 00/77233 | 12/2000 |
| WO | WO 01/11034 | 2/2001 |
| WO | WO 01/23001 | 4/2001 |
| WO | WO 01/25462 | 4/2001 |
| WO | WO 01/25465 | 4/2001 |
| WO | WO 01/27303 | 4/2001 |
| WO | WO 01/83692 | 11/2001 |
| WO | WO 01/83730 | 11/2001 |
| WO | WO 03/006616 | 1/2003 |
| WO | PCT/US2004/009950 | 3/2004 |
| WO | PCT/US2004/010045 | 3/2004 |

OTHER PUBLICATIONS

Arnold, T. et al. (1997). "In Vivo Gene Transfer into Rat Arterial Walls with Novel Adeno–Associated Virus Vectors," *J. Vascular Surgery* 25(2):347–355.

Bonthron, D. et al. (1988). "The Human von Willebrand Factor Gene. Structure of the 5' Region," *Eur. J. Biochem.* 15(171):51–57.

Gnatenko, D. et al. (1994). "Adeno–Associated Virus–2 as a Vehicle for Gene Delivery into Vascular Endothelial Cells," *Blood* 84(Supp.):741a (Abstract No. 2949).

Gnatenko, D. et al. (1996). "Generation and Characterization of Recombinant Adeno–Associated Viral (rAAV) Vectors for Factor VIII Gene Therapy," *Blood* 88(Supp.):139a (Abstract No. 543).

Gnatenko, D. et al. (1996). "Recombinant Adeno–Associated Virus–2 (rAAV) as a Vector for Gene Delivery into Vascular Cells," *J. Invest. Med.* 44(Supp.):319a (Abstract).

Gnatenko, D. et al. (1997). "Characterization of Recombinant Adeno–Associated Virus–2 as a Vehicle for Gene Delivery and Expression into Vascular Cells," *J. Invest. Med.* 45(2):87–98.

Gnatenko, D. et al. (1997). "Recombinant Adeno–Associated Virus as a Vehicle for Gene Delivery of Human Mutant Factor VIII," *Blood* 90(Supp.):119a (Abstract No. 518).

U.S. Appl. No. 09/561,190, filed Apr. 27, 2000, Lockert et al.

U.S. Appl. No. 09/578,561, filed May 25, 2000, Rasty et al.

U.S. Appl. No. 09/665,852, filed Sep. 20, 2000, Wilson et al.

U.S. Appl. No. 09/684,554, filed Oct. 6, 2000, Engelhardt et al.

U.S. Appl. No. 09/689,136, filed Oct. 12, 2000, Engelhardt et al.

U.S. Appl. No. 09/689,430, filed Oct. 12, 2000, Walsh et al.

U.S. Appl. No. 10/089,394, filed Mar. 29, 2002, Chen et al.

U.S. Appl. No. 10/375,777, filed Feb. 26, 2003, Johnson.

U.S. Appl. No. 10/615,119, filed Jul. 7, 2003, Lynch et al.

U.S. Appl. No. 10/815,262, filed Mar. 31, 2004, Engelhardt et al.

U.S. Appl. No. 10/815,557, filed Mar. 31, 2004, Engelhardt et al.

U.S. Appl. No. 10/837,029, filed Apr. 30, 2004, Engelhardt et al.

Afione, S. A. et al. (1996). "In vivo model of adeno–associated virus vector persistence and rescue" *J. Virol.* 70(5):3235–3241.

*Animal Cell Culture* R.I. Freshney, Ed., 1987.

Arispe, N. et al. (1992) "Intrinsic anion channel activity of the recombinant first nucleotide binding fold domain of the cystic fibrosis transmembrane regulator protein" *Proc. Natl. Sci. Acad. USA* 89:1539–1543.

Ashktorab, H. and A. Srivastava. (1989). "Identification of nuclear proteins that specifically interact with adeno–associated virus type 2 inverted terminal repeat hairpin DNA" *J. Virol.* 63(7):3034–3039.

Balague, C. et al. (Apr. 1997). "Adeno–associated virus Rep78 protein and terminal repeats enhance integration of DNA sequences into the cellular genome" *J. Virol.* 71(4):3299–3306.

Bassel–Duby, R. et al. (Nov. 1992). "A 40–kilodalton protein binds specifically to an upstream sequence element essential for muscle–specific transcription of the human myoglobin promoter" *Mol. Cell. Biol.* 12(11):5024–5032.

Baudard, M. et al. (Jul. 10, 1996). "Expression of the human multidrug resistance and glucocerebrosidase cDNAs from adeno–associated vectors: efficient promoter activity of AAV sequences and in vivo delivery via liposomes," *Human Gene Therapy* 7:1309–1322.

Berns, K. I. "Parvoviridae and their replication" *Virology* New York: Raven Press, 1990:1743–1763.

Berns, K. I. and R. A. Bohenzky. (1987). Adeno–associated viruses: an update *Adv. Vir. Res.* 32:243–306.

Blacklow, "Adeno–associated viruses of humans" *Paroviruses and Human Disease*. J.R. Pattinson, Ed. 1988. 165–174.

Bohenzky, R. A. et al. (1988). "Sequence and symmetry requirements within the internal palindromic sequences of the adeno–associated virus terminal repeat" *Virology* 166:316–327.

Braun, R. P. and J. S. Lee. (Sep. 15, 1988). "Immunogenic duplex nucleic acids are nuclease resistant" *J. Immunol.* 141(6):2084–2089.

Breathnach, R. and P. Chambon. (1981). "Organization and expression of eucaryotic split genes coding for proteins" *Annu. Rev. Biochem.* 50:349–383.

Carter et al. "AAV DNA replication, integration, and genetics" *Handbook of Parvoviruses vol. I*. 1989. 169–228.

Carter, B.J. (1992). "Adeno–associated virus vectors." *Curr. Opin. Biotech* 3:533–539.

Chatterjee, S. et al. "Transduction of intracellular resistance to HIV production by an adeno–associated virus–based antisense vector" *Vaccines 91*. Cold Spring Harbor Laboratory Press: 1991. 85–90.

Chatterjee, S. et al. (Nov. 27, 1992). "Dual–target inhibition of HIV–1 in vitro by means of an adeno–associated virus antisense vector" *Science* 258:1485–1488.

Chaturvedi, S. et al. (1996). "Stabilization of triple–stranded oligonucleotide complexes: use of probes containing alternating phosphodiester and stereo–uniform cationic phosphoramidate linkages" *Nucl. Acids Res.* 24(12):2318–2323.

Couture L. A. et al. (Jun. 1994). "Retroviral vectors containing chimeric promoter/enhancer elements exhibit cell–type–specific gene expression." *Human Gene Therapy* 5:667–677.

*Current Protocols in Immunology* J.E. Coligan et al. eds., 1991.

*Current Protocols in Molecular Biology* F.M. Ausubel et al. eds. 1987.

Deng, W. P. and J. A. Nickoloff. (1992). "Site–directed mutagenesis of virtually any plasmid by eliminating a unique site" *Anal. Biochem.* 200:81–88.

Dong, J. –Y.et al. (Nov. 10, 1996). "Quantitative analysis of the packaging capacity of recombinant adeno–associated virus" *Human Gene Ther.* 7:2101–2112.

Egan, M. et al. (1992). "Defective regulation of outwardly rectifying Cl– channels by protein kinase A corrected by insertion of CFTR" *Nature* 358:581–584.

Flotte, T. R. et al. (1992). "Gene expression from adeno–associated virus vectors in airway epithelial cells." *Am. J. Respir. Cell Mol. Biol.* 7(3):349–356.

Flotte, T. R. et al. (1993). "Expression of the cystic fybrosis transmembrane conductance regulator from a novel adeno–associated virus promoter." *J. Biol. Chem.* 268(5):3781–3790.

Flotte, T. R. et al. (1993). "Stable in vivo expression of the cystic fibrosis transmembrane conductance regulator with an adeno–associated virus vector." *Proc. Natl. Acad. Sci. USA* 93:10163–10167.

*Gene Transfer Vectors for Mammalian Cells*. J.M. Miller and M.P. Calos, eds. 1987.

Gottlieb J. and N. Muyczka. (Jun. 1988) "In vitro excision of adeno–associated virus DNA from recombinant plasmids: Isolation of an enzyme fraction from HeLa cells that cleaves DNA at poly(G) sequences" *Mol. Cell Biol.* 6(8):2513–2522.

*Handbook of Experimental Immunology* D.M. Weir and C.C. Blackwell, eds. 5th ed. 1996.

Hermonat, P. L. and N. Muzyczka. (Oct. 1984). "Use of adeno–associated virus as a mammalian DNA cloning vector: Transduction of neomycin resistance into mammalian tissue culture cells" *Proc. Natl. Acad. Sci. USA*, 81:6466–6470.

Hermonat, P. L. et al. (Aug. 1984) "Genetics of adeno–associated virus: Isolation and preliminary characterization of adeno–associated virus type 2 mutants" *J. Virol.* 51(2):329–339.

Im, D. –S. and N. Muzyczka. (Jul. 1989). "Factors that bind to adeno–associated virus terminal repeats" *J. Virol.* 63(7):3095–3104.

Im, D. –S. and N. Muzyczka. (May 4, 1990). "The AAV origin binding protein Rep68 is an ATP–dependent site–specific endonuclease with DNA helicase activity" *Cell* 61:447–457.

Im, D. –S and N. Muzyczka. (Feb. 1992) "Partial purification of adeno–associated virus Rep78, Rep52, and Rep40 and their biochemical characterization" *J. Virol.* 66(2):1119–1128.

Khleif, S. N. et al. (1991). "Inhibition of cellular transformation by the adeno–associated virus rep gene" *Virology* 181:738–741.

Kobayashi, M and K Kawakami. (1995) "ATF–1CREB heterodimer is involved in constitutive expression of the housekeeping Na,K–ATPase alpha 1 subunit gene" *Nucl. Acids Res.* 23(15):2848–2855.

Labow, M. A. et al. (Apr. 1987). "Adeno–associated virus gene expression inhibits cellular transformation by heterologous genes" *Moll. Cell. Biol.*7(4):1320–1325.

Latimer, L. J. P. et al. (1995). "Specificity of monoclonal antibodies produced against phosphorothioate and ribo modified DNAs" *Mol. Immunol.* 32(14):1057–1064.

Laughlin, C.A. et al. (1979). "Spliced adenovirus–associated virus RNA" *Proc. Natl. Acad. Sci. USA* 76:5567–5571.

Laughlin, C.A. et al. (1983). "Cloning of infectious adeno–associated virus genomes in bacterial plasmids" *Gene* 23:65–73.

Lebkowski et al. (Oct. 1988). "Adeno–associated virus: A vector system for efficient introduction and integration of DNA into a variety of mammalian cell types" *Mol. Cell. Biol.* 8(10):3988–3996.

LeFebvre, R. B. et al. (Jul. 1984). "Conformation takes precedence over sequence in adeno–associated virus DNA replication" *Mol. Cell Biol.* 4(7):1416–1419.

Lehner, R. et al. (Nov. 1991). "Comparative sequence analysis of human cytomegalovirus strains" *J. Clin. Microbiol.* 29(11):2494–2502.

Lu, L. et al. (1989). "Gene transfer by lipofection in rabbit and human secretory epithelial cells" *Pfluegers Arch.* 415:198–203.

Lusby, E. et al. (May 1980). "Nucleotide sequence of the inverted terminal repetition in adeno–associated virus DNA" *J. Virol.* 34(2):402–409.

McLaughlin, S.K. et al. (1988). "Adeno–associated virus general transduction vectors: analysis of proviral structures" *J. Viro* 62(6):1963–1973.

Mendelson, E. et al. (1988). "Expression and rescue of a nonselected marker from an integrated AAV vector" *Virology* 166:154–165.

*Methods in Enzymology* W.B. Jakoby and I.H. Pastan eds., Academic Press, Inc.: 1979.

Miyashita, A. et al. (1995). "Identification of a 27 bp 5'–flanking region element responsible for the low level constitutive expression of the human cytosolic phospholipase A2 gene" *Nucl. Acids Res.* 23(2):293–301.

*Molecular Cloning: A Laboratory Manual,* J. Sambrook et al., eds., 2nd ed. Cold Spring Harbor Laboratory Press: 1989.

Muro–Cacho, C.A. et al. (1992). "Gene transfer in human lymphocytes using a vector based on adeno–associated virus" *J. Immunotherapy* 11:231–237.

Muzyczka, N. (1992). "Use of adeno–associated virus as a general transduction vector for mammalian cells" *Curr. Top. Microbiol. Immunol.* 158:97–129.

Nahreini, P. and A. Srivastava. (1989). "Rescue and replication of the adeno–associated virus 2 genome in mortal and immortal human cells" *Intervirology* 30: 74–85.

Nakajima–Iijima, S. et al. (Sep. 1985). "Molecular structure of the human cytoplasmic beta–actin gene: interspecies homology of sequences in the introns" *Proc. Natl. Acad. Sci. USA* 82:6133–6137.

Ng, S. –Y. et al. (1989). "Regulation of the human beta–actin promoter by upstream and intron domains," *Nucl. Acids Res.* 17(2):601–615.

Ni, T. –H. et al. (Feb. 1994). "In vitro replication of adeno–associated virus DNA" *J. Virol.* 68(2):1128–1138.

*Oligonucleotide Synthesis* M.J. Gait Ed. 1984.

Peyrottes, S. et al. (1996). "Oligodeoxynucleoside phosphoramidates (P–NH2): synthesis and thermal stability of duplexes with DNA and RNA targets" *Nucl. Acids Res.* 24(10):1841–1848.

Ponnazhagan, S. et al. (Dec. 1995). "Transcriptional trans-activation of parvovirus B19 promoters in nonpermissive human cells by adenovirus type 2," *Journal of Virology* 69(1):8096–8101.

Quitschke, W. W. (Aug. 19, 1994). "Two nuclear factor binding domains activate expression from the human amyloid beta–protein precursor promoter" *J. Biol. Chem.* 269(33):21229–21233.

Rich, D. P. et al. (Jul. 12, 1991). "Effect of deleting the R domain on CFTR–generated chloride channels" *Science* 253:205–207.

Robinson, D. et al. (Jun. 1995). "Retroviral vector with a CMV–IE/HIV–TAR hybrid LTR gives high basal expression levels and is up–regulated by HIV–1 TAT." *Gene Therapy* 2(4):269–278.

Rose, J. A. (1974). "Parvovirus reproduction" *Comprehensive Virology*, 3:1.

Samulski, R. J. et al. (Mar. 1982). "Cloning of adeno–associated virus into pBR322: Rescue of intact virus from the recombinant plasmid in human cells" *Proc. Natl. Acad. Sci. USA* 79:2077–2081.

Samulski, R. J. et al. (May 1983). "Rescue of adeno–associated virus from recombinant plasmids: Gene correction within the terminal repeats of AAV" *Cell* 33:135–143.

Samulski, R. J. et al. (Oct. 1987). "A recombinant plasmid from which an infectious adeno–associated virus genome can be excised in vitro and its use to study viral replication" *J. Virol.* 61(10):3096–3101.

Samulski, R. J. et al. "Helper–free stocks of recombinant adeno–associated viruses: Normal integration does not require viral gene expression" 1989, *J. Virol.* 63:3822–3828.

Schultz, R. G. and S. M.Gryaznov. (1996). "Oligo–2'–fluoro–2'–deoxynucleotide N3'—>P5' phosphoramidates: synthesis and properties" *Nucleic Acids Res.* 24(15):2966–2973.

Senapathy, P. and B.J.Carter. (Apr. 10, 1984). "Molecular cloning of adeno–associated virus variant genomes and generation of infectious virus by recombinantion in mammalian cells" *J. Biol. Chem.* 259(7):4661–4666.

Senapathy, P. et al. (1984). "Replication of adeno–associated virus DNA. Complementation of naturally occurring rep–mutants by a wild–type genome or an ori– mutant and correction of terminal palindrome deletions" *J. Mol. Biol.* 179:1–20.

Sheppard, D. N. et al. (Mar. 25, 1994). "The amino–terminal portion of CFTR forms a regulated Cl–channel" *Cell* 76:1091–1098.

Smale, S. et al. (Jun. 1990). "Transcriptional activation by Sp1 as directed through TATA or initiator: Specific requirement from mammalian transcription factor IID," *Proc. Natl. Acad. Sci USA* 87:4509–4513.

Smale, S.T. and D. Baltimore. (Apr. 7, 1989). "The 'initiator' as a transcription control element" *Cell* 57:103–113.

Snyder, R. O. et al. (Jan. 12, 1990). "In vitro resolution of covalently joined AAV chromosome ends" *Cell* 60:105–113.

Srivastava, A. et al. (Feb. 1983). "Nucleotide sequence and organization of the adeno–associated virus 2 genome." *J. Virol.* 45(2):555–564.

Srivastava, A. (1987). "Replication of the adeno–associated virus DNA termini in vitro" *Intervirology* 27:138–147.

Srivastava, C. et al. (Oct. 1989). "Construction of a recombinant human parvovirus B19: Adeno–associated virus 2 (AAV) DNA inverted terminal repeats are functional in an AAV–B19 hybrid virus" *Proc. Natl. Acad.Sci. USA* 86:8078–8082.

Suzuki–Yagawa, Y. et al. (Sep. 1992). "Housekeeping Na, K–ATPase alpha 1 subunit gene promoter is composed of multiple cis elements to which common and cell type–specific factors bind" *Mol. Cell. Biol.* 12(9):4046–4055.

Tratschin, J. –D. et al. (Sep. 1984). "Genetic analysis of adeno–associated virus: Properties of deletion mutants constructed in vitro and evidence for an adeno–associated virus replication function" *J. Virol.* 51(3):611–619.

Tratschin, J. –D. et al. (Oct. 1984). "A human parvovirus, adeno–associated virus, as a eucaryotic vector: Transient expression and encapsidation of the procaryotic gene for chloramphenicol acetyltransferase" *Mol. Cell. Biol.* 4(10):2072–2081.

Tratschin, J. –D. et al. (Nov. 1985). "Adeno–associated virus vector for high–frequency integration, expression, and rescue of genes in mammalian cells" *Mol. Cell. Biol.* 5(11):3251–3260.

Tratschin, J. –D. et al. (Aug. 1986). "Negative and positive regulation in trans of gene expression from adeno–associated virus vectors in mammalian cells by a viral rep gene product" *Mol. Cell Biol.* 6(8):2884–2894.

Walsh, C. E. et al. (Aug. 1992). "Regulated high level expression of a human gamma–globin gene introduced into erythroid cells by an adeno–associated virus vector" *Proc. Natl. Acad. Sci. USA* 89:7257–7261.

Wang, D. et al. (1999). "Efficient CFTR expression form AAV vectors packaged with promoters—the second generation," *Gene Therapy* 6:667–6745.

Wang, X. –S. and A. Srivastava. (1997). "A novel terminal resolution–like site in the adeno–associated virus type 2 genome" *J. Virol.* 71(2):1140–1146.

Wang, X. –S. et al. (1995). "Rescue and replication signals of the adeno–associated virus 2 genome" *J. Mol. Biol.* 250:573–580.

Wang, X. –S. et al. (Mar. 1996) "Rescue and replication of adeno–associated virus type 2 as well as vector DNA sequences from recombinant plasmids containing deletions in the viral inverted terminal repeats: selective encapsidation of viral genomes in progeny virions" *J. Virol.* 70(3):1668–1677.

Wang, X. –S. et al. (Apr. 1997) "Adeno–associated virus type 2 DNA replication in vivo: Mutational ananlyses of the D sequence in viral inverted terminal repeats." *J. Virol.* 71(4):3077–3082.

Wonderling R. S. and R. A. Ownes, "Binding sites for adeno–associated virus rep proteins within the human genome" *J. Virol.* 71(3):2528–2534.

Wong, K.K. et al. "Restriction of HSV–1 production in cell lines transduced with an antisense viral vector targeting the ICP4 gene" *Vaccines 91*. Cold Spring Harbor Laboratory Press: 1991. 183–189.

Xiao, X. et al. (Feb. 1997). "A novel 165–base–pair terminal repeat sequence is the sole cis requirement for the adeno–associated virus life cycle" *J. Virol.* 71(2):941–948.

Zeitlin, P.L. et al. (1991). "A cystic fibrosis bronchial epithelial cell line: Immortalization by adeno–12–SV40 infection" *Am. J. Respir. Cell Mol. Biol.* 4:313–319.

* cited by examiner

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO: 1:

TCGAGTATAT AAGCAGAGCT CGTTTAGTGA ACCGTCAGAG          40

(2) INFORMATION FOR SEQ ID NO: 2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO: 2:

TCGACTCTGA CGGTTCACTA AACGAGCTCT GCTTATATAC          40

(2) INFORMATION FOR SEQ ID NO: 3:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO: 3:

TCGAGTTCTC CCTCTTCCCC TTTAATTCCA CCTTAAAACA TCTGCAAAAC          50

(2) INFORMATION FOR SEQ ID NO: 4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 4:

TCGAGTTTTG CAGATGTTTT AAGGTGGAAT TAAAGGGGAA GAGGGAGAAC                50

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 5:

TCGAGTGCAC GCTCACGCAG GTTGCTATAT AAGCAGAGCT CGTTTAGTGA ACCGTCAGA      60

(2) INFORMATION FOR SEQ ID NO: 6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 6:

TCGACTCTGA CGGTTCACTA AACGAGCTCT GCTTATATAG CAACCTGCGT GAGCGTGCA      60

(2) INFORMATION FOR SEQ ID NO: 7:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO: 7:

TCGAGGCGCC GCTAGGGGTC TCTCTCGGGT GCTATATAAG CAGAGCTCGT TTAGTGAAC      60

GTCAGAG                                                              67

(2) INFORMATION FOR SEQ ID NO: 8:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO: 8:

TCGACTCTGA CGGTTCACTA AACGAGCTCT GCTTATATAG CACCCGAGAG AGACCCCTA      60

CGGCGCC                                                              67

(2) INFORMATION FOR SEQ ID NO: 9:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (xi) SEQUENCE DESCRIPTION: SEQ ID NO: 9:

TCGAGCCGCT AGGGGTCTCT CTCGGGTGTG GGCCGGATCA GCTGACTCGC TGAGCCCCG      60

```
CGCCGCGCTC GGGCTCCGTC AG                                              82

(2) INFORMATION FOR SEQ ID NO: 10:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (xi) SEQUENCE DESCRIPTION: SEQ ID NO: 10:

TCGACTGACG GAGCCCGAGC GCGGCGGCGG GGCTCAGCGA GTCAGCTGAT CCGGCCCAC      60

CCCGAGAGAG ACCCCTAGCG GC                                              82

(2) INFORMATION FOR SEQ ID NO: 11:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (xi) SEQUENCE DESCRIPTION: SEQ ID NO: 11:

TCGAGAACGG TGACGTGCAC GCGTGGGCGG AGCCATCACG CAGGTTGCTA TATAAGCAG      60

GCTCGTTTAG TGAACCGTCA GA                                              82

(2) INFORMATION FOR SEQ ID NO: 12:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 12:

TCGACTCTGA CGGTTCACTA AACGAGCTCT GCTTATATAG CAACCTGCGT GATGGCTCC      60

CCCACGCGTG CACGTCACCG TTC                                             83

(2) INFORMATION FOR SEQ ID NO: 13:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 13:

TCGAGCTGGA GCCGGTGTCA GGTTGCTCCG GTAACGGTGA CGTGCACGCG TGGGCGGAG      60

CATCACGCAG GTTGCTATAT AAGCAGAGCT CGTTTAGTGA ACCGTCAGAG               110

(2) INFORMATION FOR SEQ ID NO: 14:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO: 14:

TCGACTCTGA CGGTTCACTA AACGAGCTCT GCTTATATAG CAACCTGAGT GATGGCTCC      60

CCCACGCGTG CACGTCACCG TTACCGGAGC AACCTGACAC CGGCTCCAGC               110
```

(2) INFORMATION FOR SEQ ID NO: 15:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 15:

```
TCGAGGCCAA TCAGCGTGCG CCGTTCCTTT TCTGGCTCGA GCGGCCCCTA TATAAGCAG      60

GCTCGTTTAG TGAACCGTCA GAG                                             83
```

(2) INFORMATION FOR SEQ ID NO: 16:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 16:

```
TCGACTCTGA CGGTTCACTA AACGAGCTCT GCTTATATAG GGGCCGCTCG AGCCAGAAA      60

GGAACGGCGC ACGCTGATTG GCC                                             83
```

(2) INFORMATION FOR SEQ ID NO: 17:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 17:

```
TCGAGCCCCA CCCCCTGCCC CACCCCCTGC CCCACCCCCT GCCCCACCCC CTGTATATA      60

GCAGAGCTCG TTTAGTGAAC CGTCAGAG                                        88
```

(2) INFORMATION FOR SEQ ID NO: 18:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 18:

```
TCGACTCTGA CGGTTCACTA AACGAGCTCT GCTTATATAC AGGGGTGGG GCAGGGGGT       60

GGGCAGGGGG TGGGGCAGGG GGTGGGGC                                        88
```

(2) INFORMATION FOR SEQ ID NO: 19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 19:

```
GCCGAGCGGG                                                            10
```

(2) INFORMATION FOR SEQ ID NO: 20:

(i) SEQUENCE CHARACTERISTICS:
        (A) LENGTH: 10 base pairs
        (B) TYPE: nucleic acid
        (C) STRANDEDNESS: single -continued

```
      (D) TOPOLOGY: linear (xi) SEQUENCE DESCRIPTION: SEQ ID NO: 20:

CCGAAAGTTG                                                                        10

(2) INFORMATION FOR SEQ ID NO: 21:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (xi) SEQUENCE DESCRIPTION: SEQ ID NO: 21:

CCTTTTCTGG                                                                        10
```

TRANSCRIPTIONALLY-ACTIVATED AAV INVERTED TERMINAL REPEATS (ITRS) FOR USE WITH RECOMBINANT AAV VECTORS

CROSS-REFERENCE TO RELATED APPLICATIONS

This application is a continuation of U.S. Ser. No. 09/171,759, filed Oct. 20, 1998 now U.S. Pat. No. 6,346,415 which is the U.S. National Phase of international application PCT/US98/21937, filed herewith on 20 Oct. 1998, which claims priority to U.S. provisional application 60/108,162 (converted from U.S. Ser. No. 08/955,400), which was filed 21 Oct. 1997.

FIELD OF THE INVENTION

This invention relates generally to the field of recombinant adeno-associated virus (AAV) vectors and preparations thereof that can be used for gene transfer.

BACKGROUND

AAV vectors are among a small number of recombinant virus vector systems which have been shown to be useful as in vivo gene transfer agents (reviewed in Carter, 1992, *Curr. Opin. Biotech.*, 3:533–539; Muzyczka, 1992, *Curr. Top. Microbiol. Immunol.* 158:97–129) and thus are potentially of great importance for human gene therapy. AAV vectors are capable of high-frequency stable DNA integration and expression in a variety of cells, including cystic fibrosis (CF) bronchial and nasal epithelial cells (see, e.g., Flotte et al., 1992, *Am. J. Respir. Cell Mol. Biol.* 7:349–356; Egan et al., 1992, *Nature*, 358:581–584; Flotte et al., 1993a, *J. Biol. Chem.* 268:3781–3790; and Flotte et al., 1993b, *Proc. Natl. Acad. Sci. USA*, 93:10163–10167); human bone marrow-derived erythroleukemia cells (see, e.g., Walsh et al., 1992, *Proc. Natl. Acad. Sci. USA*, 89:7257–7261); and several others. Unlike retroviruses, AAV does not appear to require ongoing cell division for stable integration; a clear advantage for gene therapy in tissue such as the human airway epithelium where most cells are terminally differentiated and non-dividing.

AAV is a defective parvovirus that generally replicates only in cells in which certain functions are provided by a co-infecting helper virus. General reviews of AAV may be found in Carter, 1989, *Handbook of Parvoviruses*, Vol. I, pp. 169–228; and Berns, 1990, *Virology*, pp. 1743–1764, Raven Press, New York. Examples of co-infecting viruses that provide helper functions for AAV growth and replication are adenoviruses, herpesviruses and, in some cases, poxviruses such as vaccinia. The nature of the helper function is not entirely known but it appears that an indirect effect of the helper virus is to render the cell permissive for AAV replication. This belief is supported by the observation that in certain cases AAV replication may occur at a low level of efficiency in the absence of helper virus co-infection if the cells are treated with agents that are genotoxic or that disrupt the cell cycle.

Generally, in the absence of helper virus, AAV infection results in high-frequency, stable integration of the AAV genome into the host cell genome. The integrated AAV genome can be rescued and replicated to yield a burst of infectious progeny AAV particles if cells containing an integrated AAV provirus are superinfected with a helper virus such as adenovirus. Since the integration of AAV appears to be an efficient event, AAV can be a useful vector for introducing genes into cells for stable expression for uses such as human gene therapy.

AAV has a very broad host range without any obvious species or tissue specificity and will replicate in virtually any cell line of human, simian or rodent origin, provided that an appropriate helper is present. AAV appears to be ubiquitous as it has been isolated from a wide variety of animal species, including most mammalian and several avian species.

AAV has not been associated with the cause of any disease and AAV is not a transforming or oncogenic virus. AAV integration into chromosomes of human cell lines does not cause any significant alteration in the growth properties or morphological characteristics of the cells. These properties of AAV further recommend it as a potentially useful human gene therapy vector because most of the other viral systems proposed for this application (such as retroviruses, adenoviruses, herpesviruses, or poxviruses) are disease-causing viruses.

AAV particles are comprised of a capsid having three proteins, VP1, VP2, and VP3, and enclosing a DNA genome. The AAV DNA genome is a linear single-stranded DNA molecule having a molecular weight of about $1.5 \times 10^6$ daltons or approximately 4680 nucleotides long. Strands of either sense ("plus" or "minus") are packaged into individual particles but each particle has only one DNA molecule. Equal numbers of AAV particles contain either a plus or minus strand. Virus particles containing either strand are equally infectious and replication occurs by conversion of the parental infecting single stranded DNA to a duplex form and subsequent amplification of a large pool of duplex molecules from which progeny single strands are displaced and packaged into capsids. Duplex or single-strand copies of AAV genomes inserted into bacterial plasmids or phagemids can result in infectious particles when transfected into adenovirus-infected cells, and this has allowed the study of AAV genetics and the development of AAV vectors.

In the case of subtype AAV2, the genome has two copies of a 145-nucleotide-long ITR (inverted terminal repeat), one on each end of the genome, and a unique sequence region of about 4470 nucleotides long (Srivastava et al., 1983, *J. Virol.*, 45:555–564) that contains two main open reading frames for the rep and cap genes (Hermonat et al., *J. Virol.* 51:329–339; Tratschin et al., 1984a, *J. Virol.*, 51:611–619). The unique region contains three transcription promoters, p5, p19, and p40, that are used to express the rep and cap genes. Laughlin et al., 1979, *Proc. Natl. Acad. Sci. USA*, 76:5567–5571.

ITR sequences are involved in a variety of activities in the AAV life cycle. The ITR sequences, each of which can form a hairpin structure, provide a functional origin of replication (ori) and are required in cis for AAV DNA replication and for rescue and excision from prokaryotic plasmids (Samulski et al., 1983, *Cell* 33: 135–143; Samulski et al., 1987, *J. Virol.* 61: 3096–3101; Senapathy et al., 1984, *J. Mol. Biol.* 179: 1–20; Gottlieb and Muzyczka, 1988, *Mol. Cell. Biol.* 6: 2513–2522). In addition, the ITRs appear to be the minimum sequences required for AAV proviral integration and for packaging of AAV DNA into virions (McLaughlin et al., 1988, *J. Virol.* 62: 1963–1973; Samulski et al., 1989, *J. Virol.* 63: 3822–3828; Balague et al., 1997, *J. Virol.* 71: 3299–3306). In the case of DNA replication, it is clear that most of the terminal 125 nucleotide palindrome is required for DNA replication and terminal resolution (Bohenzky et al., 1988, *Virology* 166: 316–327; LeFebvre et al., 1984, *Mol. Cell. Biol.* 4:1416–1419; Im and Muzyczka, 1989, *J. Virol.* 63: 3095–3104; Ashktorab and Srivastava, 1989, *J. Virol.* 63: 3034–3039).

Several reports indicated that ITRs generally do not behave as transcriptional regulatory sequences (Muzyczka, 1992; and Walsh et al., 1992) and the deletion of the ITR does not have a major effect on AAV p5 promoter activity (Flotte et al., 1992). Since ITRs were not thought to provide transcriptional activity, AAV vectors have been constructed using AAV promoters to express heterologous genes. See, for example, Carter et al., U.S. Pat. No. 4,797,368, issued Jan. 10, 1989. Subsequent reports by Carter and collaborators have shown ITRs to have a low amount of transcriptional activity in transient and stable expression assays. See, e.g., Carter et al. U.S. Pat. No. 5,587,308, issued Dec. 24, 1996, and Flotte et al., 1993a.

In addition to the requirement that ITR sequences be present in cis, the AAV rep and cap genes are required, in cis or in trans, to provide functions for the replication and encapsidation of the viral genome, respectively. As described below, recombinant AAV (rAAV) vectors for use in gene therapy preferably do not contain the AAV cap or rep genes, but rather these genes can be provided by a host cell used for packaging (typically referred to as an "AAV producer cell").

In the intact AAV genome, the rep gene is expressed from two promoters, p5 and p19, as noted above. Transcription from p5 yields an unspliced 4.2 kb mRNA which encodes a nonstructural protein, Rep78, and a spliced 3.9 kb mRNA which encodes a second nonstructural protein, Rep68. Transcription from p19 yields an unspliced mRNA which encodes Rep52 and a spliced 3.3 kb mRNA which encodes Rep40. Thus, the four Rep proteins all comprise a common internal region sequence but differ in their amino and carboxyl terminal regions. Only Rep78 and Rep68 are required for AAV duplex DNA replication, but Rep52 and Rep40 appear to be needed for progeny, single-strand DNA accumulation. Mutations in Rep78 and Rep68 are phenotypically Rep(-) whereas mutations affecting only Rep52 and Rep40 are Rep(+) but Ssd(-). Rep68 and Rep78 bind specifically to the ITR at sites known as RRS (Rep recognition sequences) or RBS (Rep binding sites) and the proteins possess several enzymatic activities required for resolving replication at the AAV termini. Rep52 and Rep40 have none of these properties.

The Rep proteins, primarily Rep78 and Rep68, exhibit several pleiotropic regulatory activities, including positive and negative regulation of AAV gene expression and expression from some heterologous promoters, as well as inhibitory effects on cell growth (Tratschin et al., 1986, *Mol. Cell. Biol.* 6:2884–2894; Labow et al., 1987, *Mol. Cell. Biol.,* 7:1320–1325; Khleif et al., *Virology,* 181:738–741). The AAV p5 promoter is negatively autoregulated by Rep78 or Rep68 (Tratschin et al., 1986). Perhaps because of the inhibitory effects of expression of rep on cell growth, constitutive expression of rep in cell lines has not been readily achieved. For example, Mendelson et al. (1988, *Virology,* 166:154–165) reported a very low level expression of some Rep proteins in certain cell lines after stable integration of AAV genomes.

The structural proteins VP1, VP2, and VP3 all share a common overlapping sequence but differ in that VP1 and VP2 contain additional amino terminal sequences. All three are coded from the same cap gene reading frame expressed from a spliced 2.3 kb mRNA transcribed from the p40 promoter. VP2 and VP3 are generated from the same mRNA by use of alternate initiation codons. VP1 is encoded by a minor mRNA using a 3' donor site that is 30 nucleotides upstream from the 3' donor used for the major mRNA that encodes VP2 and VP3. VP1, VP2, and VP3 are all required for capsid production. Mutations which eliminate all three proteins (Cap(-)) prevent accumulation of single-strand progeny AAV DNA whereas mutations in the VP1 amino-terminus (Lip(-), Inf(-)) permit single-strand production but prevent assembly of stable infectious particles.

The genetic analysis of AAV described above was in large part based upon mutational analysis of AAV genomes that were molecularly cloned into bacterial plasmids. In early work, molecular clones of infectious genomes of AAV were constructed by inserting double-strand molecules of the AAV genome into plasmids by procedures such as GC tailing (Samulski et al., 1982, *Proc. Natl. Acad. Sci. USA,* 79:2077–2081), addition of synthetic linkers containing restriction endonuclease sites (Laughlin et al., 1983, *Gene,* 23:65–73) or by direct, blunt-end ligation (Senapathy and Carter, 1984, *J. Biol. Chem.,* 259:4661–4666). Transfection of such AAV recombinant plasmids into mammalian cells that were also infected with an appropriate helper virus, such as adenovirus, could result in rescue and excision of the AAV genome free of any plasmid sequence, replication of the rescued genome, and generation of progeny infectious AAV particles. This provided the basis for performing genetic analysis of AAV as summarized above and permitted construction of AAV transducing vectors.

Based on the genetic analysis, the general principles of AAV vector construction were defined (for reviews, see, e.g., Carter, 1992; Muzyczka, 1992). rAAV vectors can be constructed in AAV recombinant plasmids by substituting portions of the AAV coding sequence with foreign DNA to generate a vector plasmid. In the vector plasmid, the terminal ITR portions (ITRs) of the AAV genome must be retained because of their aforementioned role in excision from the plasmid after transfection, replication of the vector genome and integration and rescue from a host cell genome. The vector can then be packaged into an AAV particle to generate an AAV transducing virus, by transfection of the vector plasmid into cells that are infected by an appropriate helper virus, such as adenovirus or herpesvirus. In order to achieve replication and encapsidation of the vector genome into AAV particles, the vector plasmid must be complemented in trans for any AAV functions, namely rep and cap, that were deleted in construction of the vector plasmid.

Several systems of using rAAV vectors to package foreign DNA and transduce it into various cells have been described. The first rAAV vectors that were described contained foreign reporter genes such as neo, cat or dhfr that were expressed from AAV transcription promoters or an SV40 promoter (Tratschin et al., 1984b, *Mol. Cell. Biol.* 4:2072–2081; Hermonat and Muzyczka, 1984, *Proc. Natl. Acad. Sci. USA,* 81:6466–6470; Tratschin et al., 1985, *Mol. Cell. Biol.* 5:3251–3260; McLaughlin et at., 1988, *J. Virol.,* 62:1963–1973; Lebkowski et at., 1988 *Mol. Cell. Biol.* 8:3988–3996). These vectors were packaged into AAV-transducing particles by co-transfection into adenovirus-infected cells together with a second packaging plasmid that contained the AAV rep and cap genes expressed from the wild-type AAV transcription promoters.

Samulski et al. (1987) constructed a plasmid, pSub201, which was an intact AAV genome in a bacterial plasmid but which had a deletion of 13 nucleotides at the extremity of each ITR and thus, was rescued and replicated less efficiently than other AAV plasmids that contained the entire AAV genome. Samulski et al. (1989) constructed other vectors based on pSub201 but deleted for rep and cap and containing either a hyg or neo gene expressed from an SV40 early gene promoter. These vectors were packaged into viral particles by co-transfection with a packaging plasmid called pAAV/Ad which consisted of the entire AAV nucleotide sequence from nucleotide 190 to 4490, enclosed at either end with one copy of an adenovirus 5 terminal repeat. In this packaging plasmid, the AAV rep and cap genes were expressed from the wild-type AAV promoters p5, p19, and p40. Since it is missing the ITRs, the AAV genome of pAAV/Ad does not appear to replicate.

Several other reports have described rAAV vectors. Srivastava et al. (1989, *Proc. Natl. Acad. Sci. USA*, 86:8078–8082) described an AAV vector, based on the pSub201 plasmid of Samulski et al. (1987), in which the coding sequences of AAV were replaced with the coding sequences of another parvovirus, B19. Since this system was based on pSub201 and it suffers from the defect described above for the pSub201 plasmid. Also, the vector and the packaging plasmid both contained the same ITR regions and thus recombination to give contaminating wild-type virus was highly likely. Chatterjee et al. (1991, *Vaccines* 91, Cold Spring Harbor Laboratory Press, pp. 85–89), Wong et al. (1991, *Vaccines* 91, Cold Spring Harbor Laboratory Press, pp. 183–189), and Chatterjee et al. (1992, *Science*, 258:1485–1488) describe rAAV vectors designed to express antisense RNA directed against infectious viruses such as HIV or Herpes simplex virus. Other reports have described the use of rAAV vectors to express genes in human lymphocytes (Muro-Cacho et al., 1992, *J. Immunotherapy*, 11:231–237) and in a human erythroid leukemia cell line (Walsh et al., 1992) with vectors based on the pSub201 vector plasmid and pAAV/Ad packaging plasmid.

Transduction of human airway epithelial cells, isolated from a cystic fibrosis patient and grown in vitro, with a rAAV vector expressing the selective marker gene neo from the AAV p5 promoter was achieved (Flotte et al., 1992). In this study, the AAVneo vector was packaged into AAV particles using the pAAV/Ad packaging plasmid.

The above-cited studies suggest that rAAV vectors may have potential utility as vectors for treatment of human disease by gene therapy. However, a severe limitation on the development of human gene therapy using rAAV vectors has been the inability to efficiently package long pieces of transgene DNA into viral capsids and to effectively express them in recipient cells. Other viral vectors, including, for example, Adenoviral vectors, also exhibit packaging size constraints, however, AAV appears to be particularly sensitive with respect to size constraints. In particular, as the optimal size is exceeded, there is a sharp and dramatic drop-off in vector production.

AAV can package a genome slightly larger than the size of a wild-type genome (about 4.6 kb). The precise relationship of genome size and efficiency of packaging has only recently been defined. Using a series of rAAV vectors with progressively increasing genome lengths, from 1.9 to 6.0 kb, Dong et al. (1996, *Human Gene Ther.* 7: 2101–2112) were able to analyze quantitatively the packaging efficiency of rAAV in relation to the vector size and to determine the size limit for packaging. Specifically, the packaging efficiencies of rAAV vectors of various sizes were determined directly by assaying DNA contents of viral particles, and indirectly by analyzing their transfer of a chloramphenicol acetyltransferase (CAT) reporter gene into target cells. Dong et al. (1996) showed that the optimal size of an rAAV vector for packaging is between 4.1 and 4.9 kb. Although AAV can package a vector larger than its genome size, including vectors up to about 5.2 kb, the packaging efficiencies in this large size range were sharply reduced. When the AAV genome size was smaller than 4.1 kb, the packaging efficiency was also suboptimal. When the size of the genome was less than half the length of the wild-type genome, two copies of the vector were packaged into each virion, suggesting that the copy number control during packaging is a "head-full" mechanism.

Dong et al. (1996) co-transfected the rAAV vectors of various sizes and the pAAV/Ad packaging plasmid (Samulski et al., 1989), into HeLa cells. AAV virions produced from the transiently transfected cells were collected and used to infect fresh HeLa cells; CAT activities in the infected cells were analyzed at 3 days post infection. The resultant CAT activity of vectors from 3.2 to 4.88 kb in length ranged from 80.7 to 129.5 cpm. However, with only a 0.2 kb increase in size beyond 4.88 kb, the resultant CAT activity dropped to 35.9 cpm, indicating a greater than 50% decrease in particle production. Further increases in size resulted in even greater decreases in particle packaging efficiency.

In sum, while recombinant rAAV vectors are believed to have utility for gene therapy, a significant obstacle has been the limitation in the amount of transgene DNA which can be efficiently packaged into viral capsids and then expressed in the recipient cells. This is a particular problem for in vivo applications which require the transfer of larger genes.

While many genes, including their native or a heterologous promoter, are small enough to fit within the size constraints of AAV packaging vectors, many others are not.

One approach to accommodate the AAV packaging constraints is to forego the use of an exogenous transcriptional promoter. In the case of the cystic fibrosis transmembrane conductance regulator (CFTR), for example, it has been shown that, even without any additional promoter, it is possible to construct and use rAAV-CFTR vectors based on the relatively low-level transcriptional activity provided by the AAV ITR itself as described by Carter and collaborators (U.S. Pat. No. 5,587,308; Flotte et al., 1993a).

Another approach is to employ transgenes which have had non-essential coding regions deleted. For example, as described by Carter et al., truncated CFTR genes in recombinant rAAV vectors have been packaged into AAV particles and used to complement the CF defect in mammalian cells. See Carter et al. U.S. patent application Ser. No. 08/455,552, now proceeding to issuance.

The aforementioned approaches exemplified by Carter et al. with regard to the CFTR gene have been quite useful and have effectively enabled the generation of rAAV vectors for use in gene therapy to treat diseases such as cystic fibrosis. Indeed, the success with these approaches has merited the initiation of two different clinical trials involving cystic fibrosis patients being sponsored by Targeted Genetics Corporation at several centers including Stanford University School of Medicine, Stanford, Calif., Johns Hopkins Children's Center, Baltimore, Md., and University of Florida, Gainesville, Fla.

There is, however, a continuing desire for improved rAAV constructs in which transgene expression can be further elevated, despite potential vector size constraints. It would be most useful to have modified rAAV vectors that provide for high efficiency particle production and enhanced expression of inserted transgenes. The present invention provides transcriptionally-activated rAAV vectors that can be employed in these contexts.

SUMMARY OF THE INVENTION

Adeno-associated virus (AAV) vectors can achieve in vivo gene transfer to any of a large variety of tissues, but AAV capsids are limited in their capacity to package DNA.

This is particularly a problem with packaging large pieces of DNA, including many therapeutic transgenes. The present invention provides for transcriptionally-activated ITRs, which can be used to optimize the expression of relatively large transgenes packaged in recombinant AAV vectors.

Embodiments of the invention include but are not limited to the following:

The invention provides, in one embodiment, a polynucleotide comprising a transcriptionally-activated Adeno-associated virus (AAV) inverted terminal repeat (ITR), wherein the tanscriptionally-activated ITR is less than about 400 bp in length and comprises a heterologous transcriptionally active element, and wherein the transcriptionally-activated ITR exhibits at least a two-fold increase (preferably at least a five fold increase) in transcriptional activity relative to a wild-type ITR under conditions permissive for transcription.

In one embodiment, the invention provides a transcriptionally-activated ITR which exhibits at least about a seven-fold increase in transcriptional activity relative to a wild-type ITR under conditions permissive for transcription, an exemplary embodiment of which comprises a transcription initiator sequence and at least one CCAC box.

In another embodiment, the invention provides a transcriptionally-activated ITR which exhibits at least about a 10-fold increase in transcriptional activity relative to a wild-type ITR under conditions permissive for transcription, an exemplary embodiment of which comprises a transcription initiator sequence and a transcriptionally active element of an amyloid β-protein precursor (APP) promoter.

In another embodiment, the invention provides a transcriptionally-activated ITR which exhibits at least about a 40-fold increase in transcriptional activity relative to a wild-type ITR under conditions permissive for transcription, an exemplary embodiment of which comprises a transcription initiator sequence and an ATF-1/CRE site and an Sp1 site.

In another embodiment, the invention provides a transcriptionally-activated ITR which exhibits at least about a 50-fold increase in transcriptional activity relative to a wild-type ITR under conditions permissive for transcription, an exemplary embodiment of which comprises a transcription initiator sequence and an ATF-1/CRE site, an Sp1 site, and a C box element of the Na,K-ATPase α1 subunit gene promoter.

The invention also provides a polynucleotide comprising, in order: a first ITR which is a transcriptionally-activated ITR, wherein the transcriptionally-activated ITR is less than about 400 bp in length and comprises a transcriptionally active element, and wherein the transcriptionally-activated ITR exhibits at least a two-fold (preferably at least a five fold) increase in transcriptional activity relative to a wild-type ITR under conditions permissive for transcription; and a second ITR selected from the group consisting of a wild-type ITR, a transcriptionally-activated ITR, a D sequence, a trs, or a portion of a wild-type ITR.

In another embodiment, the invention includes any polynucleotide of this invention further comprising a heterologous transgene operably linked to the transcriptionally-activated ITR.

In another embodiment, the invention includes any polynucleotide of this invention packaged into an AAV viral particle.

In another embodiment, the invention includes a mammalian cell comprising any polynucleotide of this invention, wherein said polynucleotide is stably integrated into a chromosome of said cell.

In another embodiment, the invention includes a method of packaging a recombinant AAV vector, comprising the steps of: providing a mammalian cell; introducing a recombinant AAV vector, said vector comprising a first ITR which is a transcriptionally-activated ITR, wherein the transcriptionally-activated ITR is less than about 400 bp in length and comprises a transcriptionally active element, and wherein the transcriptionally-activated ITR exhibits at least a two-fold (preferably at least a five fold) increase in transcriptional activity relative to a wild-type ITR under conditions permissive for transcription; and a second ITR selected from the group consisting of a wild-type ITR, a transcriptionally-activated ITR, a D sequence, a trs, or a portion of a wild-type ITR; providing Rep and Cap proteins and helper functions within the cell; and incubating the cell under conditions suitable for replication and packaging of the AAV vector.

These and other embodiments of the invention are outlined in the description that follows.

DETAILED DESCRIPTION OF THE INVENTION

Figure 1A:
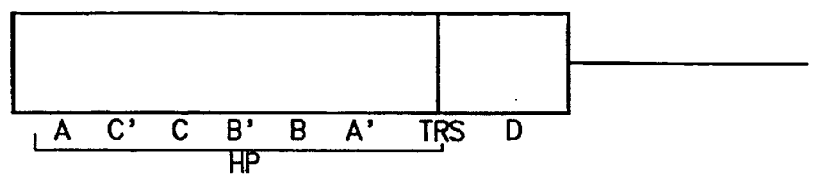
FIGS. 1A and B–E.
Figure 1B:
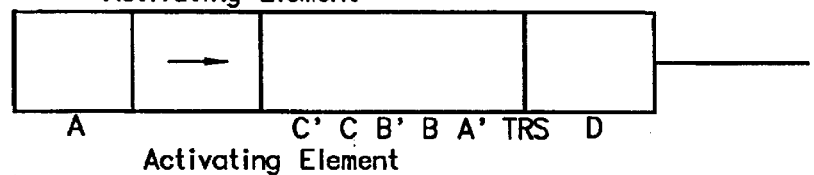
FIG. 1 diagrams regions of a wild-type ITR (in A) and examples of transcriptionally-activated ITRs of the present invention (in B–E). (HP, hairpin region; trs, terminal resolution site; D; D sequence).
Figure 1C:
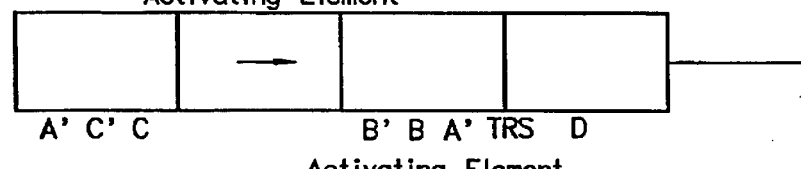
Figure 1D:
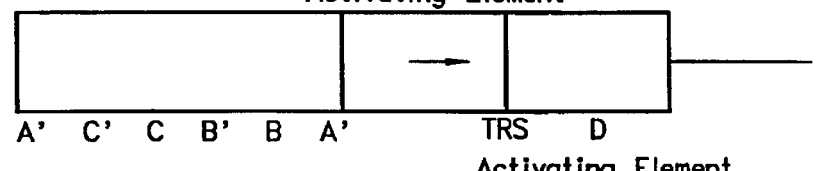
Figure 1E:
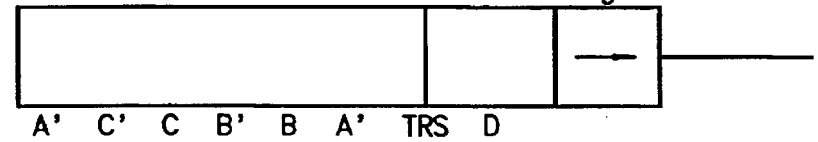

Recombinant AAV vectors are gene delivery constructs comprising a heterologous polynucleotide or "transgene" of interest flanked by at least one, and preferably two, AAV ITRs. These recombinant AAV vectors are potentially powerful tools for human gene therapy. One technical limitation associated with AAV vectors is that the capacity to package large therapeutic transgenes is constrained, as packaging and expression efficiency tends to drop dramatically as the total packaged DNA exceeds about 5 kb in length.

The invention described herein provides methods and materials for use in the production of transcriptionally-activated ITRs which maximize the transgene material that can be both packaged and expressed at high efficiency.

Definitions

"AAV" is an abbreviation for adeno-associated virus, and may be used to refer to the virus itself or derivatives thereof. The term covers all serotypes and subtypes and both naturally occurring and recombinant forms, except where required otherwise.

The term "ITR" refers to an inverted terminal repeat at either end of the AAV genome. This sequence can form hairpin structures and is involved in AAV DNA replication and rescue, or excision, from prokaryotic plasmids (Samulski et al., 1983, 1987; Senapathy et al., 1984; Gottlieb and Muzyczka, 1988). In addition, the ITRs appear to be the minimum sequences required for AAV proviral integration and for packaging of AAV DNA into virions (McLaughlin et al., 1988; Samulski et al., 1989).

The term "transcriptionally-activated ITR" or "transcriptionally-activated AAV ITR" refers to a sequence comprising nucleotide segments with considerable overall sequence identity to portions of a wild-type ITR sequence (Samulski et al., 1983, 1987; Senapathy et al., 1984; Gottlieb and Muzyczka, 1988), but which display increased transcriptional activity relative to a wild-type ITR. A transcriptionally-activated ITR of the present invention can be derived from an ITR sequence but will also carry a mutation (e.g., a deletion, inversion, substitution, addition or other change), or multiple such mutations, that renders the ITR transcriptionally-activating in that it can enhance the level of transcription of a transgene to which it is juxtaposed in an rAAV vector. The transcriptionally-activated ITR exhibits at least two-fold greater transcription promoting activity than a wild-type ITR, preferably at least five-fold, at least seven-fold, at least ten-fold, at least twenty-fold, still more preferably at least fifty-old, most preferably at least one hundred-fold greater activity. Typically, the transcriptionally active portion of the transcriptionally-activated ITR comprises sequences which have sequence similarity to a canonical sequence of a transcriptionally active element over at least 50% of the transcriptionally active portion's length, preferably at least about 90%, most preferably over the entire length. Preferably, the transcriptionally active portion of the transcriptionally-activated ITR comprises nucleotides critical for protein-nucleotide interaction, said protein(s) being involved in initiating, promoting or enhancing transcription. Generally, the ITR-derived portion of the transcriptionally-activated ITR comprises sequences which are at least 50 nucleotides long, more preferably at least 100 nucleotides long, still more preferably about 140 nucleotides long, and which have sequence similarity over at least 50% of the ITR-derived portion's length, preferably at least about 90%, most preferably over the entire length to a wild-type AAV ITR. Preferably, a transcriptionally-activated ITR would provide the variety of activities associated with a wild-type ITR, including functions in DNA replication, AAV proviral integration, packaging of AAV DNA, and excision from plasmid DNA.

The term "transcriptionally active element" or "transcriptionally active portion" refers to a sequence enabling the controlled transcription of DNA by an RNA polymerase to form RNA. Transcriptionally active elements of the present invention are generally smaller than 500 bp, preferably smaller than 200 bp, more preferably smaller than 100, most preferably smaller than 50 bp. The transcriptionally-activated ITR comprising a transcriptionally active element generally exhibits at least two-fold greater transcriptional activity than a wild-type ITR, preferably at least five-fold, at least seven-fold, at least ten-fold, at least twenty-fold, at least thirty-fold, at least forty-fold, at least fifty-fold, or at least one hundred-fold greater activity. A transcriptionally active element also contains a "transcription initiator sequence". The "transcription initiator sequence" generally determines the position of transcription initiation. Transcription initiator sequences known in the art include, for example, TATA and TATA-like boxes (see, e.g., Breathnach et al., 1981, *Annu. Rev. Biochem.* 50:349–383; Smale et al., 1989, *Cell* 57: 103–113). Thus, the transcriptionally active element includes a transcription initiator sequence (to position the start of transcription) and sequences which activate transcription to enable the controlled transcription of DNA.

The terms "polypeptide", "peptide" and "protein" are used interchangeably to refer to polymers of amino acids of any length. These terms also include proteins that are post-translationally transcriptionally-activated through reactions that include glycosylation, acetylation and phosphorylation.

"Polynucleotide" or "nucleic acid" refers to a polymeric form of nucleotides of any length, either ribonucleotides or deoxyribonucleotides, or analogs or derivatives thereof. This term refers only to the primary structure of the molecule. Thus, double- and single-stranded DNA, as well as double- and single-stranded RNA, and RNA-DNA hybrids are included. It also includes transcriptionally-activated polynucleotides such as methylated or capped polynucleotides. In addition, a "polynucleotide" or "nucleic acid" includes any polymer comprising purine and pyrimidine bases, or other natural, chemically or biochemically transcriptionally-activated bases or contain non-natural or derivatized nucleotide bases. The backbone of the polynucleotide can comprise sugars and phosphate groups, or transcriptionally-activated or substituted sugar or phosphate groups. Alternatively, the backbone of the polynucleotide can comprise a polymer of synthetic subunits such as phosphoramidates and thus can be a oligodeoxynucleoside phosphoramidate or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. In another embodiment, a phosphorothiate linkage can be used in place of a phosphodiester linkage. Braun et al. (1988) *J. Immunol.* 141: 2084–9; Latimer et al. (1995) *Mol. Immunol.* 32:1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

"Recombinant," as applied to a polynucleotide, means that the polynucleotide is the product of cloning, restriction endonuclease and/or ligation steps, or any combination of these steps or other procedures that result in a polynucleotide construct that is distinct from a polynucleotide found in nature.

"Sequence overlap" between two polynucleotides occurs when the nucleotides share a homologous sequence of sufficient length and identity that recombination is facilitated. The level of homology and corresponding frequency of recombination increase with increasing length of the homologous sequences and with their level of shared identity. In the context of the present invention, it is preferred that the rAAV vector not exhibit substantial sequence overlap with AAV rep and/or cap genes that are provided in trans to promote AAV replication and encapsidation (thereby reducing the frequency at which replication-competent AAV vectors might be generated). The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination.

A "vector" refers to a recombinant plasmid or virus that comprises a polynucleotide to be delivered into a host cell, either in vitro or in vivo.

A "recombinant AAV vector" or "rAAV vector" refers to a vector comprising one or more heterologous (i.e. non-AAV) polynucleotides of interest that are flanked by at least one, preferably two, AAV ITRs. A single ITR may be sufficient for replication of an rAAV vector under some circumstances. rAAV vectors can be replicated and packaged into infectious viral particles when present in a host cell that has been infected with a suitable helper virus and is expressing the AAV rep and cap genes.

An "AAV virus" or "AAV viral particle" refers to a particle comprising an AAV capsid and an encapsidated polynucleotide.

A "transgene" is a polynucleotide to be delivered to cells via a vector and can comprise a coding sequence of interest in gene therapy. This may also be referred to as a "target polynucleotide" or a "therapeutic transgene".

The terms "ITR-derived element", "ITR-derived sequence" and the like indicate a wild-type ITR or any other portion of an ITR which is capable of promoting rescue, replication and encapsidation functions of the ITR and which can therefor be incorporated into a modified ITR of the present invention.

AAV "rep" and "cap" genes encode replication and encapsidation proteins, respectively, and have been found in all AAV serotypes examined. Typically, the rep and cap genes are found adjacent to each other in the AAV genome, and they are generally conserved among AAV serotypes. These functions can be, and typically are, provided in trans in the context of rAAV production, as illustrated below.

A "helper virus" for AAV refers to a second virus that allows wild-type AAV (which is generally a defective parvovirus) to be replicated and packaged by a host cell. A number of such helper viruses have been identified, including adenoviruses, herpesviruses and poxviruses such as vaccinia. Helper virus functions refer to those functions of a helper virus which promote and/or facilitate AAV production, which functions can be isolated from helper virus and used independently in the context of AAV production.

"Packaging" as used herein refers to a series of intracellular events that results in the assembly and encapsidation of an AAV genome or an rAAV vector. Thus, when a suitable vector plasmid is introduced into a packaging cell line under appropriate conditions, it will be assembled into a vector viral particle.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a transcriptionally active element that is removed from its native coding sequence and operably linked to a different coding sequence is a heterologous transcriptionally active element.

"Operably linked" refers to a juxtaposition, wherein the components so described are in a relationship permitting them to function in their intended manner. A transcriptionally active element is operably linked to a coding sequence if the transcriptionally active element promotes transcription of the coding sequence. An operably linked transcriptionally active element is usually in cis configuration with the coding sequence, but is not necessarily contiguous with it.

"Host cells", "cell lines", "cell cultures", and other such terms denote higher eukaryotic cells, most preferably mammalian cells, which can be used as recipients for recombinant vectors or other transfer polynucleotides, and include the progeny of the original cell that was transduced. It is understood that the progeny of a single cell are not necessarily completely identical in morphology or in genomic complement to the original parent cell.

"Stable integration" of a polynucleotide into a cell means that the polynucleotide has been introduced into a chromosome or mini-chromosome of the cell and, therefore, becomes a relatively permanent part of the cellular genome. Although episomes, such as plasmids, can sometimes be maintained for many generations (particularly if kept under selective pressure), genetic material carried episomally is generally more susceptible to loss than chromosomally-integrated material. Also, the chromatin structure of eukaryotic chromosomes can influence the level of expression of an integrated polynucleotide. Such chromatin-induced effects can diminish or enhance the relative degree to which an integrated polynucleotide is expressed. Typically, a number of integrated clones are produced and clones exhibiting desirable levels of expression under production conditions are selected.

"Efficiency" when used in describing viral production, replication or packaging refers to useful properties of the method; in particular, the growth rate and the number of virus particles produced per cell. "High efficiency" production indicates production of at least 100 viral particles per cell; preferably at least about 10,000 and more preferably at least about 100,000 particles per cell, over the course of the culture period specified in the method.

General Techniques

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed, 1984), *Animal Cell Culture* (R. I. Freshney, Ed., 1987), the series *Methods in Enzymology* (Academic Press, Inc.); *Gene Transfer Vectors for Mammalian Cells* (J. M. Miller and M. P. Calos eds. 1987), *Handbook of Experimental Immunology*, (D. M. Weir and C. C. Blackwell, Eds.), *Current Protocols in Molecular Biology* (F. M. Ausubel, R. Brent, R. E. Kingston, D. D. Moore, J. G. Siedman, J. A. Smith, and K. Struhl, eds., 1987), and *Current Protocols in Immunology* (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

Modes of Carrying Out the Invention

AAV capsids are useful for delivering transgene DNA to target cells, but are limited in their capacity to package DNA, particularly large pieces of DNA, such as those exceeding about 5.0 kb. The present invention provides for tanscriptionally-activated ITRs, which, due to their activity and small size, can effectively increase the amount of transgene DNA that can be packaged in and efficiently expressed from an rAAV vector. According to the present invention, ITRs are transcriptionally-activated by the inclusion of transcriptional control sequences, such as a transcriptionally active element, that enhances transcription of the adjoining transgene. Several examples of how transcriptionally-activated ITRs can be configured are diagrammed in FIG. 1, as described in detail below.

Thus, an rAAV vector of the present invention can be prepared by constructing, in sequence, a transcriptionally-activated ITR, a transgene (in place of the bulk or entirety of the AAV genomic coding region), and a second ITR-derived element sufficient for replication and packaging. The second ITR-derived element can comprise a wild-type ITR, a D sequence of an ITR, a trs, or any portion of an ITR sufficient to allow replication, rescue and packaging. The length of the rAAV vector is preferably between about 4.1 and 5.2 kb, more preferably between 4.2 and 5.2 kb, more preferably between 4.3 and 5.1 kb, most preferably between 4.6 and 5.0 kb.

The rAAV vector can be located on a plasmid which can also comprise any or all of the following elements: reporter gene(s), origin of replication, additional promoters, multiple cloning sites, as is known in the art and illustrated in the various references cited herein.

AAV of any serotype or subtype are suitable, since the various serotypes are functionally and structurally related, even at the genetic level (see, e.g., Blacklow, pp. 165–174 of "Parvoviruses and Human Disease" J. R. Pattison, ed., 1988; and Rose, *Comprehensive Virology* 3:1, 1974). All AAV serotypes apparently exhibit similar replication properties mediated by homologous rep genes; and all bear three related capsid proteins such as those expressed by AAV2. The degree of relatedness is further suggested by heteroduplex analysis which reveals extensive cross-hybridization between serotypes along the length of the genome; and the presence of analogous self-annealing segments at the termini that correspond to ITRs. Similar infectivity patterns also suggest that the replication functions in each serotype are under similar regulatory control. Among the available serotypes, AAV2 is presently preferred.

Various methods for the generation and processing of AAV particles in mammalian cells have been described. It is typical to employ a host or "producer" cell for rAAV vector replication and packaging. Such a producer cell (usually a mammalian host cell) generally comprises or is modified to comprise several different types of components for rAAV production. The first component is an rAAV vector genome (or "rAAV pro-vector") that can be replicated and packaged into vector particles by the host packaging cell. The rAAV pro-vector will normally comprise a transgene. The transgene is generally flanked by two ITRs which comprise sequences that are recognized during excision, replication and packaging of the AAV vector, as well as during integration of the vector into a host cell genome. As described in the present invention, transcriptionally-activated ITRs further comprise sequences that promote the efficient expression of the operably linked transgene. A second component is a helper virus that can provide helper functions for AAV replication. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order. The final components for AAV production to be provided in the producer cell are "AAV packaging genes" such as AAV rep and cap genes that provide replication and encapsidation proteins, respectively. Several different versions of AAV packaging genes can be provided (including wild-type rep-cap cassettes as well as modified rep and/or cap cassettes in which the rep and/or cap genes can be left under the control of the native promoters or operably linked to heterologous promoters. Such AAV packaging genes can be introduced either transiently or stably into the host packaging cell, as is known in the art and described below.

One exemplary technique for the generation of high titers of recombinant AAV vectors is outlined by Targeted Genetics Corporation and Johns Hopkins University in U.S. Pat. No. 5,658,776 (Flotte et al.). This example uses a mammalian cell with at least one intact copy of a stably integrated rAAV vector, wherein the vector comprises an AAV ITR and a transcription promoter operably linked to a target polynucleotide, but wherein the expression of rep is limiting. In a preferred embodiment, an AAV packaging plasmid comprising the rep gene operably linked to a heterologous AAV is introduced into the cell, and then the cell is incubated under conditions that allow replication and packaging of the AAV vector sequence into particles.

A second exemplary technique is outlined in patent application WO 95/13392 (Trempe et al.) and corresponding U.S. patent application Ser. No. 08/362,608 (now proceeding to issuance). This example uses a stable mammalian cell line with an AAV rep gene operably linked to a heterologous promoter so as to be capable of expressing functional Rep protein. In various preferred embodiments, the AAV cap gene can be provided stably as well or can be introduced transiently (e.g. on a plasmid). A recombinant AAV vector can also be introduced stably or transiently.

Another exemplary technique is outlined in patent application WO 96/17947 (by Targeted Genetics Corporation, J. Allen). This example uses a mammalian cell which comprises a stably integrated AAV cap gene, and a stably integrated AAV rep gene operably linked to a heterologous promoter that is inducible by helper virus. In various preferred embodiments, a plasmid comprising the vector sequence is also introduced into the cells (either stably or transiently). The rescue of AAV vector particles is then initiated by introduction of the helper virus.

After culturing the host cells under conditions that permit AAV replication and encapsidation, the cells and sub-cellular fractions can be processed to generate high titer preparations of adeno-associated virus (AAV) that are substantially free of helper virus, helper virus proteins, and cellular proteins. An exemplary technique is outlined in U.S. patent application Ser. No. 08/925,815 for the generation of high titer rAAV preparations that are substantially free of helper virus, helper virus proteins, and cellular proteins and other components.

These various examples address the issue of providing AAV at sufficiently high titer, minimizing recombination between vector and packaging components, and reducing or avoiding the potential difficulties associated with the expression of the AAV rep gene in mammalian cell line (since the Rep proteins can not only limit their own expression but can also affect cellular metabolism). An example is also provided of a technique for the production of AAV virus substantially free of helper virus that can be employed for the large-scale production of recombinant AAV vector preparations.

Additional methods for producing high titers of rAAV particles are described in various commonly-owned U.S. patent applications including U.S. Patent Application No. 60/041,609 (Burstein); U.S. Patent Application No. 60/041,689; and U.S. patent application Ser. No. 08/955,232, filed Oct. 21, 1997 (Lynch et al.).

Anatomy of ITRs

Wild-type AAV ITRs provide a functional origin of replication (ori) and function in cis for AAV DNA replication and for rescue or excision from prokaryotic plasmids (Samulski et al., 1983; Samulski et al., 1987; Senapathy et al., 1984; Gottlieb and Muzyczka, 1988). Although ITRs were not generally thought to behave as transcriptional regulatory sequences (Carter, 1990; Muzyczka, 1992; and Walsh et al., 1992; Flotte et al., 1992), wild-type ITRs have been shown to provide a low level of transcriptional activity (Carter et al. U.S. Pat. No. 5,587,308; Flotte et al., 1993a).

In the case of AAV2, the wild-type ITRs are 145 nucleotides long (Srivastava et al., 1983). An ITR comprises two regions, the hairpin (HP) region and the D sequence. The HP sequence comprises the terminal 125 nucleotides of the AAV2 ITR, while the D sequence comprises the adjoining 20 nucleotides. In addition, the terminal resolution site (trs) lies between the HP region and the D sequence.

The HP region contains palindromic sequence elements in the order A, C', C, B', B, A', and thus can fold back on itself to form a T-shaped hairpin structure (FIG. 1). Muzyczka, 1992. The terminal HP structure is apparently used as a primer for initiation of viral DNA replication, converting the single-stranded genome into a double-stranded template with a covalently closed hairpin at one end (Berns and Bohenzky, 1987, *Adv. Vir. Res.* 32: 243–306; Lusby et al., 1980, *J. Virol.* 34: 402–409; Nabreini and Srivastava, 1989, *Intervirology* 30: 74–85; Ni et al., 1994, *J. Virol.* 68: 1128–1138; Srivastava, 1987, *Intervirology* 27: 138–147).

The D sequence, which is not involved in forming the T-shaped structure of the ITR, appears to play a crucial role in high-efficiency rescue, selective replication and encapsidation of the AAV genome. Wang et al., 1997, *J. Virol.* 71: 3077–3082. Analysis of several D sequence mutants has shown that, when the 10 nucleotides of the D sequence distal to the HP were removed, the AAV genome could undergo efficient rescue, replication and encapsidation. However, when the deletion was extended to 15 nucleotides, rescue, replication and packaging were severely compromised. Wang et al., 1997. A host cell protein, designated D sequence-binding protein (D-BP), specifically interacts with the D sequence. Wang et al., 1996, *J. Virol.* 70: 1668–1677.

The trs lies at the junction of the D sequence and HP sequences. The trs appears to be specifically bound and cleaved by Rep78 and Rep68. Ashktorab and Srivastava, 1989; Im and Muzyczka, 1989; Im and Muzyczka, 1990, *Cell* 61: 447–457; Im and Muzyczka, 1992, *J. Virol.* 66: 1119–1128; Snyder et al., 1990, *Cell* 60: 105–113. Rep-mediated cleavage at the trs appears to be independent of the D sequence. Wang et al., 1996.

Transcriptionally-activated ITRs

Not all of the ITR appears to be essential for its various functions. For example, the 10 nucleotides of the D sequence distal to the HP region can apparently be deleted without impairing rescue, replication and encapsidation. See, e.g., Wang et al., 1997. However, much of the terminal 125 nucleotides of the HP region appears to be needed for DNA replication and terminal resolution (Bohenzky et al., 1988; LeFebvre et al., 1984; Im and Muzyczka, 1989; Ashktorab and Srivastava, 1989).

A transcriptionally-activated ITR of this invention can comprise all or portions of a wild-type ITR that has been transcriptionally-activated by inclusion of at least one transcriptionally active element. Various types of transcriptionally active elements are suitable for use in this context. Constitutive transcriptionally active elements provide an ongoing level of gene transition, and are preferred when it is desired that the transgene be expressed on an ongoing basis. Inducible transcriptionally active elements generally exhibit low activity in the absence of an inducer (or inducing condition), and are up-regulated in the presence of the inducer (or switch to an inducing condition). They may be preferred when expression is desired only at certain times or at certain locations, or when it is desirable to titrate the level of expression using an inducing agent. Transcriptionally active elements may also be tissue-specific; that is, may they exhibit their activity only in certain tissues or cell types, presumably due to gene regulatory elements or factors found uniquely in those cells.

Transcriptionally active elements, can be incorporated into an ITR in a variety of ways (see FIG. 1 for illustrative examples). For example, a transcriptionally active element can be incorporated 5' to any portion of an ITR (e.g. 5' to the HP region, or 5' to the trs) or 3' to any portion of an ITR (e.g., 3' to the B' region of the HP or 3' to the D sequence). Alternately, a transcriptionally active element of a transcriptionally-activated ITR may lie between two ITR sequences (e.g., between segments B and B' of the HP or between segments C' and A'). If the transcriptionally active element comprises two or more elements which must be spaced apart, those elements may alternate with portions of the ITR (e.g., one transcriptionally active element may lie between B and B', while another element lies between C and C'). Alternatively, a hairpin structure of the ITR can be deleted and replaced with inverted repeats of a transcriptional element; this latter arrangement would create a hairpin mimicking the deleted portion in structure. Multiple tandem transcriptionally active elements can also be present in a transcriptionally-activated ITR, and these may be adjacent or spaced apart. In addition, protein binding sites (e.g. Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the rAAV in a relatively limited nucleotide sequence length which effectively maximizes the length of a transgene which can be carried and expressed from the rAAV vector. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicate the functional elements of the transcriptionally active element. A number of techniques exist in the art to efficiently add, delete, and/or change particular nucleotide sequences at specific sites (see, for example, Deng and Nickoloff (1992) *Anal. Biochem.* 200:81–88).

Another way to create transcriptionally-activated ITRs is described in the Examples below. Generation of the transcriptionally-activated ITRs involved the introduction of a restriction site at a desired location in the ITR. Complementary oligonucleotides comprising the transcriptionally activate element were annealed to one another such that the ends generated were compatible with the aforementioned restriction site in the ITR. The double-stranded transcriptionally-activated element and restriction-digested ITR were ligated together to create the transcriptionally-activated ITRs. This approach can also be used to incorporate multiple transcriptionally activate elements into a transcriptionally-activated ITR.

Cryptic trs sequences can provide another method of further reducing the ITR sequences necessary for replication. A cryptic trs in the p5 promoter may substitute for replication if the left end ITR is completely deleted. Wang et al., 1995, *J. Mol. Biol.* 250: 573–580; Wang et al., 1996. In addition, Xiao et al. (1997, *J. Virol.* 71: 941–948) have shown that only 165 nucleotides of the AAV genome (comprising two copies of the D sequence, a unique sequence adjacent to the AAV nicking site and only one ITR) appear to be sufficient for replication when Rep and helper functions are provided in trans. Thus, an AAV vector of the present invention may comprise only a single ITR and an additional sequence such as a D sequence or trs, one or more of which is modified by the inclusion of a transcription activating element. Noncritical sequences (e.g., "wobble" bases; or spacer or transmembrane segments without strict requirements for amino acid sequence) within or at the C-terminus of the transgene can be altered to mimic sequences of a trs or D sequence, thereby further reducing the amount of AAV sequence required in an AAV vector.

By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ box, APBα box, CArG box, CCAC box, or any other element involved in transcription as known in the art. Many other transcriptionally active elements are known and new such elements are regularly identified. Many such sequences are available as, or contained within, plasmids and can be obtained from the ATCC depository or commercial sources. The transcriptional activity of new elements can be tested using standard techniques in which sequence elements are placed adjacent to promoterless "reporter" genes using procedures analogous to those described and illustrated in detail below.

It is also possible to remove small transcription activating sequences from larger promoters. Exemplary promoters include: the immediate early promoter from cytomegalovirus (CMV), the SV40 late promoter from simian virus 40, Herpes Simplex Virus thymidine kinase (HSV tk), and various retroviral promoters including LTR elements. Examples of inducible promoters include heavy metal ion inducible promoters (such as the mouse mammary tumor virus (MMTV) promoter or growth hormone promoter), and the promoters from T7 phase which are active in the presence of T7 RNA polymerase. Examples of tissue specific promoters include the albumin promoter (for expression in the liver) or the surfactin promoter (for expression in the lung).

A variety of transcriptionally-activated ITRs of different transcriptional activities are thus provided by the present invention. For some applications, one practicing the present invention may desire the maximal level of transcription of a transgene. In such a case, the practitioner may select a transcriptionally-activated ITR which provides the greatest transcriptional level. For others applications, a more modest transcription of the transgene may be desired. For example, a transcription level equivalent to two to five times that of a wild-type ITR may be optimal if the product of the transgene is slightly toxic and/or a relatively low level of transcription is sufficient for therapeutic purposes. In such a case, the practitioner may select a transcriptionally-activated ITR which provides the desired (but not necessarily maximal) level of transcription.

The appropriate level of transcription, and thus transgene expression, will be determined by practitioners with regard to the particular gene therapy. Typically, where the gene therapy is being performed to correct for a missing or defective gene, levels of transgene expression that approximate those of the wild-type gene are selected. For other cases, higher levels of expression may prove to be more beneficial.

The transcriptional activity of a transcriptionally-activated ITR can thus be determined by the transcriptionally active element(s) incorporated into the ITR. Combinations of transcriptionally active elements can influence transcriptional activity in ways distinct from those elements when used alone. The spacing and orientation of the transcriptionally active elements relative to each other can also influence their combined transcriptional activity. Demonstrated in Example 2 is an example of increased transcriptional activity when an additional element was incorporated into a tanscriptionally-activated ITR (compare results of rAAV with transcriptional element 6 to those of rAAV with transcriptional element 7).

Modulation of transcriptional activity from transcriptionally-activated ITRs can also be accomplished through changes in the nucleotide sequences of the transcriptionally active element The function of transcriptionally active elements generally depends on the binding of regulatory proteins that specifically recognize the nucleotide sequence of the element. Alterations in the protein-binding sites of the transcriptionally active element (i.e., nucleotide insertion, deletion, or substitution) could effect the binding efficiency of the protein. For example, an alteration in the sequence of an element that would lead to a higher binding affinity between the protein and its recognition sequence may result in increased transcription. Methods to introduce site-directed alterations at specific nucleotide sequences are well known to those of skill in the art. Protein-binding domains within nucleotide sequences can be determined through assays such as eletrophoretic mobility shift assay, DNase protection assay, methylation-interfences assay, as well as others known in the art.

To test the transcriptional activity of the transcriptionally-activated ITR, it can be joined to a reporter gene polynucleotide that encodes an easily assayable enzymatic activity, as illustrated in Example 2. The chloramphenicol acetyltransferase (CAT) "reporter" gene provides a means to measure the transcriptional activity of a transcriptionally-activated ITR relative to that of the wild-type ITR. As illustrated below, cells in culture were transiently transfected with the transcriptionally-activated ITR-reporter gene constructs and, after an appropriate culture period, the amount of CAT activity in the cells determined. The amount of CAT activity driven from the transcriptionally-activated ITRs relative to that from the wild-type ITR is graphically presented in FIG. 2. This test can be performed in the type of cell most appropriate for the transgene. Numerous other promoterless reporter genes have been described and are widely available, including, e.g., genes encoding β-galactosidase and luciferase. Alternatively, the transcriptional activity of the transcriptionally-activated ITRs linked to the transgene of interest can be determined through the direct measurement of transgene mRNA produced by the transfected cells or by the quantitation of transgene-encoded polypeptide produced by the cells.

One of skill in the art can readily determine if the introduction of a transcriptionally active element into an ITR impairs replication, packaging, integration, rescue or other IR functions. For example, a comparison of packaging efficiency or expression levels of a reporter gene (such as an antibiotic resistance marker or a gene producing a detectable product, as luciferase or β-galactosidase), as is known in the art, can be performed to compare otherwise isogenic AAV packaging vectors, one of which comprises a wild-type ITR, the other comprising a transcriptionally-activated ITR.

Producing the Packaging Cell Line

The parental lines from which packaging cells are generated can be obtained from any cell line that is susceptible to AAV infection, and amenable to culture in vitro. As noted earlier, AAV has a very broad host range and has been isolated from a variety of mammalian cell types, including simian, human and rodent cells. For human gene therapy, human cell lines in which appropriate helper functions can be expressed are typically preferred. For example, such human cell lines from which the packaging cell lines may be derived, include HeLa, A549, 293, KB, Detroit, and WI38 cells. IB3 cells, a human bronchial epithelial cell line, were selected for demonstration of the transcriptional activity of various transcriptionally-activated ITRs of the present invention.

Generating rAAV Vectors

To generate recombinant AAV (rAAV) particles useful for such purposes as gene therapy, the packaging cell line is supplied with a recombinant AAV vector comprising a transcriptionally-activated ITR and a target polynucleotide. The rAAV vector may also comprise a transcriptionally-activated ITR, an additional promoter (or promoters), and the target polynucleotide. The target polynucleotide is operably linked to a transcriptionally active portion of a transcriptionally-activated ITR or the additional promoter. Any of a variety of genes that are missing, defective, or expressed at low levels in association with a disease condition are candidates for incorporation into rAAV vectors.

By way of illustration, a rAAV vector can comprise a transcriptionally-activated ITR operably linked to a polynucleotide that encodes a functional cystic fibrosis transmembrane conductance regulator polypeptide (CFR) operably linked to a promoter. As is now known in the art, there are a variety of CFTR polypeptides that are capable of reconstructing CFTR functional deficiencies in cells derived from cystic fibrosis patients. As described in the commonly-owned U.S. patent application Ser. No. 08/445,552 (which is proceeding to issuance), a truncated CFTR polypeptide, missing amino acids 1–118 of the wild-type protein, was able to restore a cAMP-regulated chloride ion conductance in cells with the cystic defect (IB3 cells). The portion of the CFTR cDNA that encodes amino acids 1–118 was deleted from the full cDNA so that the polynucleotide could be packaged into a rAAV. Analogously, Rich et al. (1991, *Science* 253: 205–207) described a CFTR derivative missing amino acid residues 708–835, that was capable of transporting chloride and capable of correcting a naturally occurring CFTR defect. To take two additional examples, Arispe et al. (1992, *Proc. Natl. Acad. Sci. USA* 89: 1539–1543) showed that a CFTR fragment comprising residues 433–586 was sufficient to reconstitute a correct chloride channel in lipid bilayers; and Sheppard et al. (1994, *Cell* 76: 1091–1098) showed that a CFTR polypeptide truncated at residue 836 to about half its length was still capable of building a regulated chloride channel. Thus, the native CFTR protein, and mutants and fragments thereof, all constitute CFTR polypeptides that are useful under this invention.

While the term "ITR" implies that two ITRs present on the same AAV genome be inverted relative to each other, in the present invention the two ITRs need not be perfect inversions of each other. In the present invention, for example, an AAV vector may comprise a transcriptionally-activated ITR on one end, and an identical or non-identical ITR-derived sequence on the other (see FIG. 2B for illustrative examples). This ITR-derived sequence may be the same transcriptionally-activated ITR, a different transcriptionally-activated ITR, a wild-type ITR, a D sequence, a trs, or any other portion of an ITR which is capable of complementing a transcriptionally-activated ITR to allow rescue, replication and encapsidation functions. Wang et al., 1995; Wang et al., 1996; Xiao et al., 1997.

Other useful target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme, such as the wild-type p53 tumor suppressor cDNA for replacement of the missing or damaged p53 gene associated with some lung and breast cancers; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy.

The rAAV vector can also contain a positive and/or negative selectable marker in order to allow for selection of cells that have been infected by the rAAV vector.

Since the therapeutic specificity of the resulting recombinant AAV vector is determined by the plasmid introduced, the same packaging cell line can be used for any of these applications. The plasmid comprising the specific target polynucleotide is introduced into the packaging cell for production of the rAAV vector by one of several possible methods; including, for example, electroporation.

Helper virus can be introduced before, during or after introduction of the rAAV vector. The plasmid can be co-infected into the culture along with the helper virus. The cells are then cultured for a suitable period, typically 2–5 days, in conditions suitable for replication and packaging as known in the art (see references below). Lysates are prepared, and the recombinant AAV vector particles are purified by techniques known in the art, preferably using the techniques described by Targeted Genetics Corporation in a U.S. patent application Ser. No. 08/925,815 filed Sep. 5, 1997 (Atkinson et al.)

In a preferred embodiment the recombinant AAV vector comprising the transcriptionally-activated ITR is itself stably integrated into a clone of the packaging cell line. Such a stable, vector-containing packaging line can be grown and stored until ready for use. To induce production of rAAV particles, the user simply infects the cells with helper virus and cultures the cells under conditions suitable for replication and packaging of AAV. Methods for the production of high titers of rAAV particles have been described in U.S. Pat. No. 5,658,776; WO 95/13392; WO 96/17947; U.S. patent application Ser. No. 60/041,609; U.S. Patent Application 60/041,689; U.S. patent application Ser. No. 08/955,232.

Through the combination of transcription promoting activity with endogenous ITR functions in a very small sequence, the transcriptionally-activated ITRs of this invention provide a means to maximize the length of target gene polynucleotide sequence that can be encapsidated into a rAAV particle and also a means to support transcriptional activity of the target polynucleotide once it is incorporated into the host cell genome. This invention describes a method by which the DNA sequence of an ITR can be transcriptionally-activated such that, in addition to the endogenous functions associated with an ITR, the transcriptionally-activated ITR can provide regulatory elements to activate transcription of an operably-linked target gene. A large number of transcriptionally active regulatory elements are known in the art. The activity of such elements can be effected by many factors including nucleotide sequence, the presence or absence of other elements, the spacing between such elements, and the relative element orientation. Not every transcriptional activating element will perform as desired in the ITR context, but these can be readily generated and tested, as illustrated in Example 2, to identify those modified ITRs exhibiting a desirable level of transcriptional activity. Illustrated in Example 2 are examples of transcriptionally-activated ITRs that provide varying levels of transcriptional activity within the context of a functional AAV ITR. Additionally, rAAV vectors with such transcriptionally-activated ITRs retain the ability to be efficiently packaged into infectious viral particles (Example 3).

The examples presented below are provided as a further guide to the practitioner of ordinary skill in the art, and are not to be construed as limiting the invention in any way.

EXAMPLES

Example 1

Construction of Transcriptionally-activated ITRs for AAV Vectors

By way of illustration, a series of transcriptionally-activated ITRs have been constructed. All transcriptionally active elements were constructed using pairs of complementary oligonucleotides with the defined sequences. Typically, when the complementary oligonucleotides were annealed, XhoI-compatible ends were generated.

Example 1-1

Transcriptional Element 1: TATA Box/CMV Sequence (40-bp)

```
oligonucleotide 1 (SEQ ID NO:1):
5'TCGAGTATATAAGCAGAGCTCGTTTAGTGAACCGTCAGAG 3' oligonucleotide 2 (SEQ ID NO:2):
5'TCGACTCTGACGGTTCACTAAACGAGCTCTGCTTATATAC 3'
```

The double underlined sequence is derived from an element of the CMV promoter. Lehner et al., 1991, *J. Clin. Microbiol.* 29: 2494–2502. It includes the TATA box (bold, italics) and the sequences up to and including the transcriptional start site.

This transcriptional element was not cloned into the AAV-CAT vector but this sequence is a subsequence of other TATA box-containing transcriptional elements described below.

Example 1-2

Transcriptional Element 2: 27-bp Element (Phospholipase A2 Gene) with InR (Synthetic Initiation Region)(50-bp)

```
oligonucleotide 1 (SEQ ID NO:3):
5'TCGAGTTCTCCCTCTTCCCCTTTAATTCCACCTTAAAACATCTGCAAAAC 3' oligonucleotide 2 (SEQ ID NO:4):
5'TCGAGTTTTGCAGATGTTTTAAGGTGGAATTAAAGGGGAAGAGGGAGAAC 3'
```

This element is derived from the cytosolic phospholipase A$_2$ (cPLA$_2$) gene promoter and contains no TATA box. Miyashita et al., 1995, *Nucleic Acids Res.* 23: 293–301. Transcriptional element 2 comprises the 27-nucleotide fragment, along with adjoining sequences, in total comprising sequences from −30 to +14 (underlined) relative to the major transcriptional start site of the cPLA$_2$ gene. Extra sequence at the ends of the oligonucleotides form the sticky ends of a XhoI restriction site. The fragment also contains the sequence CTCCCTCT (bold), which is similar (mismatch underlined) to the initiator element (CTCANTCT) of the terminal deoxynucleotidyltransferase (TdT) gene. Smale et al., 1989.

Example 1-3

Transcriptional Element 3: CRE site+TATA Box (60-bp)

```
oligonucleotide 1 (SEQ ID NO:5):
5'TCGAGTGCACGCTCACGCAGGTTGCTATATAAGCAGAGCTCGTTTAGTGAACCGTC AGAG 3' oligonucleotide 2 (SEQ ID NO:6):
5'TCGACTCTGACGGTTCACTAAACGAGCTCTGCTTATATAGCAACCTGCGTGAGCGT GCAC 3'
```

This transcriptional element contains only the cAMP regulatory element (CRE) and sequences to space it from the TATA box (bold, italics). This CRE site is from the Na,K-ATPase α1 subunit (Atp1 α1) gene promoter. Suzuki-Yagawa et al., 1992, *Mol. Cell. Biol.* 12: 4046–4055; Kobayashi et al., 1995, *Nucleic Acids Res.* 23: 2848–2855. These sequences are fused to the CMV TATA box and transcriptional initiation site (double underlined). Lehner et al., 1991.

Example 1-4

Transcriptional Element 4: APBβ+TATA Box (67-bp)

```
oligonucleotide 1 (SEQ ID NO:7):
5'TCGAGGCGCCGCTAGGGGTCTCTCTCGGGTGCTATATAAGCAGAGCTCGTTTAGTGAACCGTCAGAG 3' oligonucleotide 2 (SEQ ID NO:8):
5'TCGACTCTGACGGTTCACTAAACGAGCTCTGCTTATATAGCACCCGAGAGAGACCC CTAGCGGCGCC 3'
```

The sequence from nucleotides 5 to 32 of oligonucleotide 1 (SEQ ID NO:7) (single underlined) is from a portion of the human amyloid β-protein precursor (APP) promoter and includes a nuclear factor binding domain, the APBβ box (bold), as defined by Quitschke, 1994, *J. Biol. Chem.* 269: 21229–21233. At least 70–90% of the total activity of the APP promoter in HeLa and PC-12 cells can be attributed to the binding domain APBβ. While the APP promoter is apparently devoid of CCAAT or TATA boxes, in the present transcriptional element includes sequences derived from the TATA box (bold, italics) and transcriptional start site from the CMV promoter (nucleotides 33 to 66, double-underlined). Lehner et al., 1991.

Example 1-5
Transcriptional Element 5: APBα/APBβ+InR (82-bp)

```
oligonucleotide 1 (SEQ ID NO:9):
5'TCGAGCCGCTAGGGGTCTCTCTCGGGTG()TGGGCCGGATCAGCTGAC
TCG(())CTGAGCCCCGCCGCCGCGCTCGGGCTCCGTCAG 3' oligonucleotide 2 (SEQ ID NO:10):
5'TCGACTGACGGAGCCCGAGCGCGGCGGCGGGGCTCAGCGAGTCAGCTG
ATCCGGCCCACACCCGAGAGAGACCCCTAGCGGC 3'
```

Like transcriptional element 4 above, the sequence of transcriptional element 5 is derived from the human amyloid β-protein precursor (APP) promoter. Quitschke, 1994. Transcriptional element 5 contains the APBβ (bold), APBα (bold italics) and the InR sequences. However, it differs from the endogenous APP promoter in that a 10-nucleotide sequence {ΔGCCGAGCGGG (SEQ ID NO:19), indicated by "o"} between APBβ and APBα and a 7-nucleotide sequence (ΔCCTGGCT, indicated by "(o)") near APBα were deleted to keep the transcriptional element within an acceptable size range. Deletion of the 10 nucleotides between APBβ and APBα apparently had no effect on promoter activity. Quitschke, 1994.

Example 1-6
Transcriptional Element 6: ATF-1/CRE/Sp1+TATA Box (83-bp)

```
oligonucleotide 1 (SEQ ID NO:11):
5'TCGAGAACGGTGACGTGCACGCGTGGGCGGAGCCATCACGCAGGTTGC
TATATAAGCAGAGCTCGTTTAGTGAACCGTCAGAG 3' oligonucleotide 2 (SEQ ID NO:12):
5'TCGACTCTGACGGTTCACTAAACGAGCTCTGCTTATATAGCAACCTGC
GTGATGGC TCCGCCCACGCGTGCACGTCACCGTTC 3'
```

This transcriptional element is derived from the Na,K-ATPase α1 subunit gene promoter and includes the ATF-1/CRE site (bold) and an Sp1 site (underline). Suzuki-Yagawa et al., 1992; Kobayashi et al., 1995. The ATF-1/CRE site has been shown to bind nuclear factors and is apparently required for efficient transcription of the Na,K-ATPase α1 subunit gene. Kobayashi et al., 1995. The sequence is fused to the CMV TATA box (bold, italics) and transcriptional start site.

Example 1-7
Transcriptional Element 7: ATF-1/CRE/Sp1+TATA Box (110-bp)

```
oligonucleotide 1 (SEQ ID NO:13):
5'TCGAGCTGGAGCCGGTGTCAGGTTGCTCCGGTAACGGTGACGTGCACG
CGTGGGCGGAGCCATCACGCAGGTTGCTATATAAGCAGAGCTCGTTTAGT
GAACCGTCAGAG 3' oligonucleotide 2 (SEQ ID NO:14):
5'TCGACTCTGACGGTTCACTAAACGAGCTCTGCTTATATAGCAACCTGA
GTGATGGCTCCGCCCACGCGTGCACGTCACCGTTACCGGAGCAACCTGAC
ACCGGCTCCAGC 3'
```

This transcriptional element includes a larger region of the Na,K-ATPase α1 subunit gene promoter than transcriptional element 6. Transcriptional element 7 contains the element of construct 6 above and also includes additional sequences from the same promoter found to bind nuclear proteins, C boxes (bold). Suzuki-Yagawa et al., 1992. This sequence is again fused to the CMV TATA box (bold, italics) and transcription initiation region (double underlined).

Example 1-8
Transcriptional Element 8: CArG Box/CCAAT Box/TATA Box (83-bp)

```
oligonucleotide 1 (SEQ ID NO:15):
5'TCGAGGCCAATCAGCGTGCGCCGTT-CCTTTTCTGGCTCGAGCGGCCC
CTATATAAGCAGAGCTCGTTTAGTGAACCGTCAGAG 3' oligonucleotide 2 (SEQ ID NO:16):
5'TCGACTCTGACGGTTCACTAAACGAGCTCTGCTTATATAGGGGCCGCT
CGAGCCAG AAAAGGAACGGCGCACGCTGATTGGCC 3'
```

This transcriptional element contains a sequence derived from that comprising the CCAAT box (italics) and the CArG box (bold) from the human β-actin gene (underlined). Nakajima-Iijima et al., 1985, Proc. Natl. Acad. Sci. U.S.A. 82: 6133–6137. A CArG box comprises the sequence CCW$_6$GG, where W is A or T. This transcriptional element differs from that of the published sequence in that a 10-bp deletion {ΔCCGAAAGTTG (SEQ ID NO:20), designated by "–"} has been introduced between the CCAAT box and the CArG box, and an A to C mutation has been made at one position CCTTTTCTGG (SEQ ID NO:21) (underlined). This sequence was fused to a sequence (double underlined) comprising the CMV TATA box (bold, italics) and transcriptional start site. In the wild-type human β-actin gene promoter, the CArG box is separated from a putative TATA box by 23 nucleotides; in this transcriptional element these elements are separated by 15 nucleotides.

Example 1-9
Transcriptional Element 9: CCAC Box$_4$/TATA Box (88-bp)

```
oligonucleotide 1 (SEQ ID NO:17):
5'TCGAGCCCCACCCCCTGCCCCACCCCCTGCCCCACCCCCTGCCCCACC
CCCTGTATATAAGCAGAGCTCGTTTAGTGAACCGTCAGAG 3' oligonucleotide 2 (SEQ ID NO:18):
5'TCGACTCTGACGGTTCACTAAACGAGCTCTGCTTATATACAGGGGTG
GGGCAGG GGGTGGGGCAGGGGGTGGGGCAGGGGGTGGGGC 3'
```

This transcriptional element contains four copies of a CCAC box (bold) from the muscle-specific, human myoglobin promoter as defined by Bassel-Duby et al., 1992, Mol. Cell. Biol. 12: 5024–5032. However, it has been described that repeats of a sequence containing the CCAC box function in a variety of cell types. The CCAC box used here is a smaller version than previously published. The repeated sequence is fused to a segment (double underlined) comprising the CMV TATA box (bold, italics) and transcriptional start site.

Example 1-10
Use of Exemplary Transcription Elements to Generate Modified ITRs To construct transcriptionally-activated ITRs, complementary oligonucleotides comprising various transcriptionally active elements as described above were annealed (forming XhoI-compatible ends), kinased, and the segments were cloned into the XhoI site of an AAV-CAT vector. The XhoI site was engineered immediately 3' of the upstream ITR (at base pair 146), thus placing the transcriptionally active element in combination with an ITR and forming a transcriptionally-activated ITR. The AAV-CAT vector contains the same 5' untranslated sequence, poly A signal and XhoI cloning site as the AAV-CFTR vector described in Afione et al., 1996, J. Virol. 70:3235–3241. The AAV-CAT vector, however, does include the 37 nucleotides of AAV wild type sequence prior to the 3' (downstream) ITR. The cloning places the transcriptionally-activated ITR into operable linkage with the CAT gene.

Example 2
Testing Transcriptional Activity of AAV CAT Vectors Containing Transcriptionally-activated ITRS The ability of the transcriptionally-activated ITRs to drive transcription of the CAT reporter gene was tested in the CFBE IB3-1 cell line (IB3 cells), a human bronchial epithelial cell line, derived from a CF patient and immortalized with an adeno/SV40 hybrid virus. Luo et al. 1989, *Pfluegers Arch.* 415: 198–203; Zeitlin et al. 1991, *Am. J. Respir. Cell Mol. Biol.* 4: 313–319.

These AAV CAT vectors with transcriptionally-activated ITRs were transfected into IB-3 cells. Forty-eight hours after transfection, cell extracts were prepared and CAT activity was measured as the amount (%) of $^{14}$C-Chloramphenicol which was acetylated by incubation with 50 μL of cell extract (equivalent to $5\times10^5$ cells) at 37° C. for 16 hours followed by separation of the acetylated and unacetylated substrate by silica gel thinlayer chromatography and scintillation counting to determine radioactivity (Sambrook et al., 1989)

Figure 2:
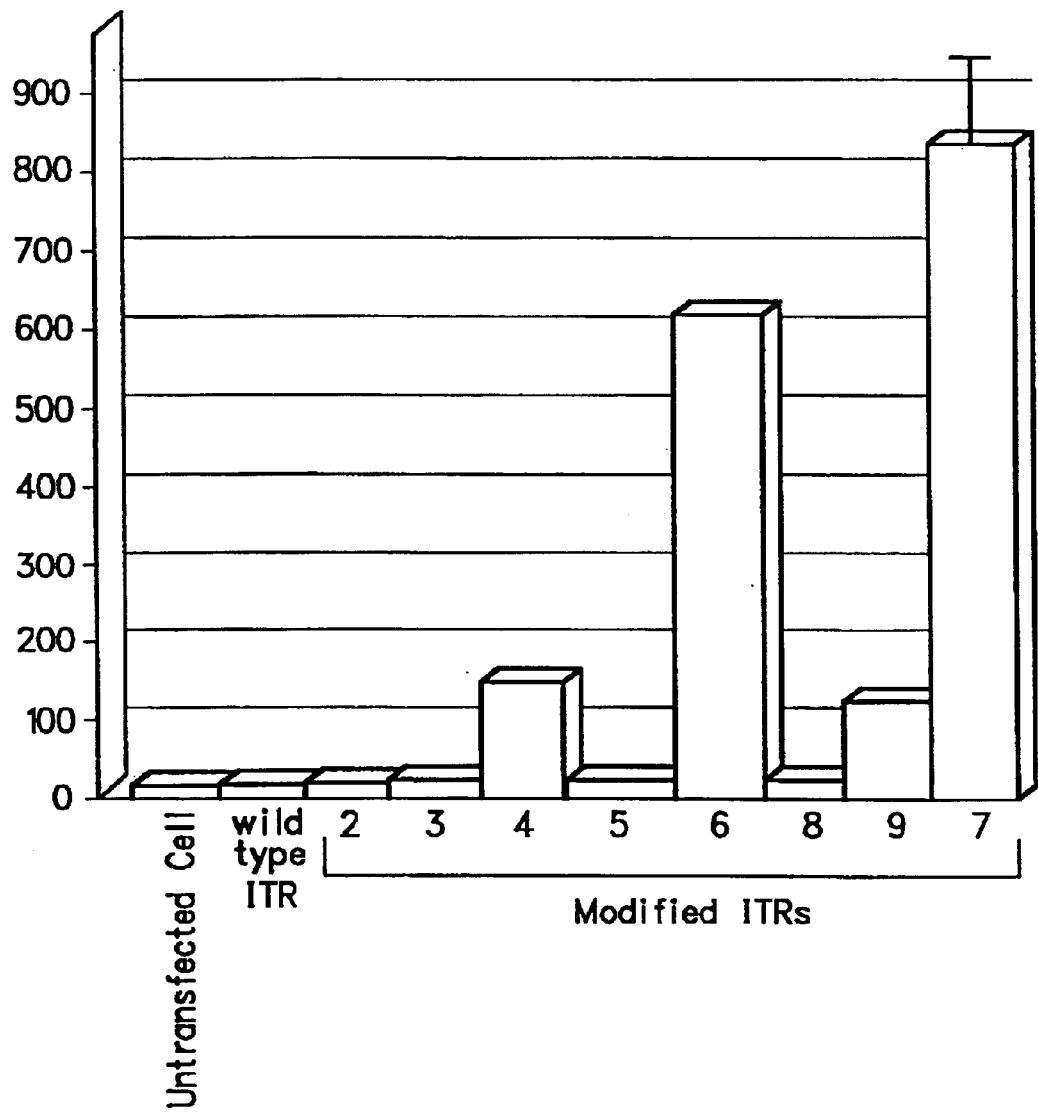
FIG. 2. CAT activity after tansfection with AAV CAT vectors containing transcriptionally-activated ITRs. The bar graph indicates CAT activity in IB3 cells transfected with various AAV CAT vectors. CAT activity is displayed relative to that from cells transfected with an AAV CAT vector containing a wild-type ITR. This data is based on an average of three transient tansfections with each vector. Standard deviations are indicated with error bars.

The CAT activity generated from the various transcriptionally-activated ITR containing AAV CAT vectors is presented relative to that generated from the delta 37 AAV CAT vector, a vector in which transcription of the CAT gene depends solely on an ITR. An ITR is thought to have a low level of transcriptional promoter activity (Carter et al. U.S. Pat. No. 5,587,308; Flotte et al., 1993a). The results are depicted in FIG. 2 and summarized below.

|  | Add'l length | CAT activity (relative to wild-type ITR) |
|---|---|---|
| 0. ITR alone | (-) | background |
| 1. TATA Box | 40-bp | (n/a) |
| 2. 27-bp element (phospholipase A2 gene) with InR | 50-bp | ≅2.0 X |
| 3. CRE site + TATA Box | 60-bp | ≅2.0 X |
| 4. APBβ + TATA Box | 67-bp | ≅9.1 X |
| 5. APBα/APBβ + InR | 82-bp | ≅2.0 X |
| 6. ATF-1/CRE/Sp1 + TATA box | 83-bp | ≅37.7 X |
| 7. ATF-1/CRE/Sp1/C + TATA box | 110-bp | ≅51.0 X |
| 8. CArG box/CCAAT box/TATA box | 83-bp | ≅2.0 X |
| 9. CCAC box$_4$/TATA box | 88-bp | ≅7.8 X |

As shown above, the disclosed transcriptionally-activated ITRs provided various levels of transcriptional activities, ranging from about a 2-fold increase or less over that of the wild-type ITR (the background level), to about a 7-fold increase over background, to about a 10-fold increase, to about a 40-fold increase, to greater than about a 50-fold increase.

Thus, various transcriptionally active elements encompassed by this invention may be useful for inducing low, moderate or high levels of expression of desired gene products.

Transcriptionally active elements either longer than those described herein, or shorter than those described herein, can be used in the present invention.

The more active transcriptionally active elements generally comprised a TATA box and an additional transcriptionally active element derived from components of the APBβ, ATF-1/CRE/Sp1, ATF-1/CRE/Sp1/C, and CCAC box$_4$ or other segments or binding sites. Other transcriptionally active elements comprising similar sets of components can be used in this invention, even if the nucleotide sequence is not identical to those disclosed herein. For example, many analogous elements can be identified and obtained from other promoters. In addition, changes can be made between essential elements of the promoter or within essential elements provided that those changes do not hinder the activity of the essential elements (e.g., substitutions in the TATA box region which do not greatly reduce transcriptional activity are known in the art). Alternatively, if a low level of transcription is desired, specific changes may be made in essential elements to decrease transcriptional activity to a desired level (e.g., using substitutions in the TATA box known in the art to decrease transcriptional activity).

Example 3

Production of Virus Particles from AAV CFTR Vectors with Transcriptionally-activated ITRs The transcriptionally-activated ITRs that demonstrated various elevated levels of transcriptional activity in the AAV CAT vectors were cloned upstream of the CFTR cDNA, as in the tgAAVCFTR vector of Afione et al. (1996). Illustrative rAAV CFTR vectors were thus generated with transcriptionally-activated ITRs containing transcriptionally active elements 4 (APBβ+TATA box), 6 (ATF-1/CRE/Sp1+TATA box), 7 (ATF-1/CRE/Sp1/C+TATA box), and 9 (CCAC box$_4$+TATA box). Virus preparations were made from these four vectors as well as from the parental vector, which contains a wild-type ITR and the CFTR cDNA.

For virus preparation, T225 flasks of JIc12 cells were transiently transfected with each vector using the DEAE-dextran transfection method. The cells were harvested 72 hours post-transfection by scraping the cells from the flasks and resuspending them at $5\times10^6$ cells/ml in TMEG (50 mM Tris, pH 8.0, 5 mM MgCl$_2$, 1 mM EDTA, 5% glycerol) plus 100 mM NaCl. The cells were lysed by a freeze/thaw cycle followed by sonication (4×15 second bursts). The cell lysate was benzonase treated for 1 hour at 37° C. and then filtered through a 5.0 micron Millex SV filter. The rAAV virus particles were purified on a single column. Fractions containing rAAV virus particles were pooled and dialyzed.

The number of DNase-resistant rAAV particles was determined by a slot blot assay as follows. Aliquots of samples were denatured in 0.4M NaOH, 10 mM EDTA with 1.0 μg/ml salmon sperm DNA at 65° C. Samples and adenovirus standards were diluted and filtered onto nylon membranes using a slot blot manifold and washed with 0.4M NaOH.

The filter was hybridized with a $^{32}$P-labeled probe corresponding to the adenovirus E1A gene sequence. The entire Ad5 genome is available on Genbank at accession number X02996. A probe comprising the 1.0 kb SspI-XbaI fragment (corresponding to nucleotides 339–1339) was used and the blots were analyzed on a phosphorimager (Molecular Dynamics). One genome equivalent was considered to be equivalent to one adenovirus particle.

The number of infectious rAAV particles was determined by the following C37 replication assay. HeLa C37 was constructed to allow inducible expression of AAV Rep proteins for rAAV vector replication. Briefly, an AAV Rep/Cap expression cassette consisting of the mouse metallothionein I promoter, AAV2 rep and cap genes and AAV transcription termination site was constructed. Also included in the plasmid was a neomycin resistance gene under the control of the SV40 early promoter, SV40 small T intron and the SV40 polyadenylation signal. HeLa cells were transfected with the plasmid and clones were selected in G418. A panel of clones was screened by a rAAV vector amplification assay. One clone, C37, demonstrated consistent and dose-dependent amplification of rAAV vector following transduction and adenovirus infection.

Detection of replicating vector is accomplished by DNA isolation followed by hybridization to a CFTR probe. In detail, HeLa C37 cells were inoculated at $4.4\times10^4$ cells/cm$^2$ in tissue culture flasks with DMEM supplemented with 10% FBS and 2.0 mM L-glutamine and incubated for twenty-four hours at 37° C. in a humidified incubator at 5% $CO_2$. The cells were then inoculated with adenovirus (MOI=5) and dilutions of rAAV sample for 72 hours. Cells were harvested by scraping and prepared for Southern blot analysis. Total cellular DNA was prepared, digested with EcoRI, electrophoresed on a 1% agarose gel, transferred to a nylon 66 membrane followed by hybridization with a $^{32}$P-labeled human CFTR cDNA restriction fragment. This probe detects an approximately 1.5 kb fragment from the AAV CFTR vector. Vector replication was quantitated relative to an endogenous genomic CFTR band and is expressed as replication units. One replication unit (RU) is defined as a signal intensity equivalent to that of the endogenous genomic CFTR band which is approximately 1.8 kb. In some experiments, linear regression of serially diluted known vector standards was used to extrapolate and calculate vector concentration in samples.

The results from both assays indicate that there is no significant differences between the parental ITR AAV CFTR virus preparation and the transcriptionally-activated ITR AAV CFTR virus preparations with regard to virus particle production.

These results demonstrated that modifications can be made to AAV ITRs that significantly increase their transcriptional activity without interfering with the packaging or the production of infectious viral particles from the rAAV vectors. Such transcriptionally-activated ITRs can thus be useful for the preparation of rAAV vectors that can deliver a transgene that can be expressed at enhanced levels.

Example 4

Construction of AAV Vectors with Transcriptionally-activated ITRs

A recombinant AAV vector of the present invention may be prepared by constructing, in sequence, a transcriptionally-activated ITR, a target polynucleotide, and a second ITR element sufficient for replication and packaging. The transcriptionally-activated ITR should be operably linked to the target polynucleotide. The second ITR element may comprise a wild-type ITR, a D sequence of an ITR, a trs, or any portion of an ITR sufficient to allow replication, rescue and packaging. The length of the AAV vector is ideally between about 4.2 and 5 kb.

The AAV vector may be located on a plasmid which may also comprise any or all of the following elements: reporter gene(s), origin of replication, additional promoters, multiple cloning sites, etc.

What is claimed is:

1. A polynucleotide comprising a region containing an Adeno-associated virus (AAV) inverted terminal repeat (ITR) and one or more heterologous transcriptionally active elements incorporated 3' with respect to the ITR, wherein the transcriptional activity is increased at least about two-fold relative to a polynucleotide containing the ITR and lacking the one or more heterologous transcriptionally active elements under conditions permissive for transcription, wherein at least one of the one or more heterologous transcriptionally active elements is a transcriptionally active element from a human gene, and wherein the region containing the ITR and the one or more transcriptionally active elements is less than about 400 nucleotides in length.

2. A polynucleotide according to claim 1 wherein the region containing the ITR and the one or more transcriptionally active elements is less than about 200 nucleotides.

3. A polynucleotide according to claim 1 wherein the transcriptional activity is increased at least about seven-fold relative to a polynucleotide containing the ITR and lacking the one or more transcriptionally active elements under conditions permissive for transcription.

4. A polynucleotide according to claim 3 wherein the region containing the ITR and the one or more transcriptionally active elements comprises a transcription initiator sequence and at least one CCAC box.

5. A polynucleotide according to claim 4 wherein the transcription initiator sequence and at least on CCAC box are contained within a polynucleotide segment less than about 90 nucleotides.

6. A polynucleotide according to claim 5 wherein the one or more transcriptionally active elements have at least about 90% overall identity to SEQ ID NO:17, or the sequence complementary thereto.

7. A polynucleotide according to claim 4 wherein the region containing the ITR and the one or more transcriptionally active elements comprises SEQ ID NO:17.

8. A polynucleotide according to claim 1 wherein the transcriptional activity is increased at least about 10-fold relative to a polynucleotide containing the ITR and lacking the one or more transcriptionally active elements under conditions permissive for transcription.

9. A polynucleotide according to claim 1 wherein the region containing the ITR and the one or more transcriptionally active elements comprises a transcriptionally active element of an amyloid β-protein precursor (APP) promoter and a transcription initiator sequence.

10. A polynucleotide according to claim 9 wherein the transcriptionally active element of an amyloid β-protein precursor (APP) promoter and the transcription initiator sequence are contained within a polynucleotide segment less than about 70 nucleotides.

11. A polynucleotide according to claim 10 wherein the transcriptionally active element has at least about 90% overall sequence identity to SEQ ID NO:7, or the sequence complementary thereto.

12. A polynucleotide according to claim 9 wherein the region containing the ITR and the one or more transcriptionally active elements comprises SEQ ID NO:7.

13. A polynucleotide according to claim 1 wherein the transcriptional activity is increased at least about 40-fold relative to a polynucleotide containing the ITR and lacking the one or more transcriptionally active elements under conditions permissive for transcription.

14. A polynucleotide according to claim 1 wherein the transcriptional activity is increased at least about 50-fold relative to a polynucleotide containing the ITR and lacking the one or more transcriptionally active elements under conditions permissive for transcription.

15. A polynucleotide according to claim 1 further comprising a gene operably linked to the region containing the ITR and transcriptionally active elements.

16. A polynucleotide of claim 15, wherein the gene is a CFTR gene.

17. A polynucleotide comprising a region containing an Adeno-associated virus (AAV) inverted terminal repeat (ITR) and a heterologous segment incorporated 3' with respect to the ITR, wherein the heterologous segment comprises one or more transcriptionally active elements, wherein the transcriptional activity is increased at least about two-fold relative to a polynucleotide containing the ITR and lacking the heterologous segment under conditions permissive for transcription, wherein the heterologous segment is less than 500 nucleotides in length and is tissue specific, and wherein the heterologous segment has a deletion compared to its native sequence.

18. A polynucleotide according to claim 17 wherein the heterologous segment is less than 200 nucleotides.

19. A polynucleotide according to claim 17 wherein the heterologous segment is less than 100 nucleotides.

20. A polynucleotide according to claim 17 wherein at least one of the transcriptionally active elements is tissue specific.

21. A polynucleotide according to claim 17 further comprising a gene operably linked to the region containing the ITR and transcriptionally active elements.

22. A polynucleotide of claim 21 wherein the gene is a CFTR gene.

23. A polynucleotide comprising a region containing an Adeno-associated virus (AAV) inverted terminal repeat (ITR) and a heterologous segment incorporated 3' with respect to the ITR, wherein the heterologous segment comprises one or more transcriptionally active elements which are removed from a promoter, wherein the transcriptional activity is increased at least about two-fold relative to a polynucleotide containing the ITR and lacking the heterologous segment under conditions permissive for transcription, and wherein the heterologous segment is less than 500 nucleotides in length and is tissue specific.

24. A polynucleotide according to claim 23 wherein the heterologous segment is less than 200 nucleotides.

25. A polynucleotide according to claim 23 wherein the heterologous segment is less than 100 nucleotides.

26. A polynucleotide according to claim 23 wherein at least one of the transcriptionally active elements is tissue specific.

27. A polynucleotide according to claim 23 further comprising a gene operably linked to the region containing the ITR and transcriptionally active elements.

28. A polynucleotide of claim 27, wherein the gene is a CFTR gene.

29. A polynucleotide comprising, in order:
a region containing a first AAV ITR and one or more heterologous transcriptionally active elements incorporated 3' with respect to the ITR, wherein the transcriptional activity is increased at least about two-fold relative to a polynucleotide containing the ITR and lacking the one or more transcriptionally active elements under conditions permissive for transcription, wherein at least one of the one or more heterologous transcriptionally active elements is a transcriptionally active element from a human gene, and wherein the region containing the ITR and the one or more transcriptionally active elements is less than about 400 nucleotides in length; and
a second AAV ITR selected from the group consisting of a wild-type ITR, a transcriptionally-activated ITR, a D sequence, a trs, or a portion of a wild-type ITR.

30. A polynucleotide according to claim 29 wherein the region containing the ITR and the one or more transcriptionally active elements is less than about 200 nucleotides.

31. A polynucleotide according to claim 29 further comprising a gene operably linked to the region containing the ITR and the one or more heterologous transcriptionally active elements.

32. A polynucleotide according to claim 31, wherein the gene is a CFTR gene.

33. A plasmid comprising a polynucleotide of claim 29, further comprising an element selected from the group consisting of an origin of replication and a reporter gene.

34. An AAV viral particle comprising a polynucleotide of claim 29.

35. An AAV viral particle according to claim 34, wherein the polynucleotide is between 4600 nucleotides and 5000 nucleotides in length.

36. A polynucleotide comprising, in order:
a region containing a first AAV ITR and a heterologous segment incorporated 3' with respect to the ITR, wherein the heterologous segment comprises one or more transcriptionally active elements, wherein the transcriptional activity is increased at least two-fold relative to a polynucleotide containing the ITR and lacking the heterologous segment under conditions permissive for transcription, wherein the heterologous segment is less than 500 nucleotides in length and is tissue specific, and wherein the heterologous segment has a deletion compared to its native sequence; and
a second AAV ITR selected from the group consisting of a wild-type ITR, a transcriptionally-activated ITR, a D sequence, a trs, or a portion of a wild-type ITR.

37. A polynucleotide of claim 36, wherein the starting site of the first AAV ITR and the ending site of the second AAV ITR are contained within a polynucleotide segment between 4600 nucleotides and 5000 nucleotides in length.

38. A polynucleotide of claim 36, wherein the heterologous segment is less than 200 nucleotides.

39. A polynucleotide of claim 36, wherein at least one of the transcriptionally active elements is tissue specific.

40. A polynucleotide of claim 36, further comprising a gene operably linked to the region containing the ITR and the heterologous segment.

41. A polynucleotide of claim 40, wherein the gene is a CFTR gene.

42. A plasmid comprising a polynucleotide of claim 36, further comprising an element selected from the group consisting of an origin of replication and a reporter gene.

43. An AAV viral particle comprising a polynucleotide of claim 36.

44. An AAV viral particle according to claim 43, wherein the polynucleotide is between 4600 nucleotides and 5000 nucleotides in length.

45. A polynucleotide comprising, in order:
a region containing a first AAV ITR and a heterologous segment incorporated 3' with respect to the ITR, wherein the heterologous segment comprises one or more transcriptionally active elements which are removed from a promoter, wherein the transcriptional activity is increased at least two-fold relative to a polynucleotide containing the ITR and lacking the heterologous segment under conditions permissive for transcription, and wherein the heterologous segment is less than 500 nucleotides in length and is tissue specific; and
a second AAV ITR selected from the group consisting of a wild-type ITR, a transcriptionally-activated ITR, a D sequence, a trs, or a portion of a wild-type ITR.

46. A polynucleotide of claim 45, wherein the starting site of the first AAV ITR and the ending site of the second AAV ITR are contained within a polynucleotide segment between 4600 nucleotides and 5000 nucleotides in length.

47. A polynucleotide of claim 45, wherein the heterologous segment is less than 200 nucleotides.

48. A polynucleotide of claim 45, wherein at least one of the transcriptionally active elements is tissue specific.

49. A polynucleotide of claim 45, further comprising a gene operably linked to the region containing the ITR and the heterologous segment.

50. A polynucleotide of claim 49, wherein the gene is a CFTR gene.

51. A plasmid comprising a polynucleotide of claim 45, further comprising an element selected from the group consisting of an origin of replication and a reporter gene.

52. An AAV viral particle comprising a polynucleotide of claim 45.

53. An AAV viral particle according to claim 52, wherein the polynucleotide is between 4600 nucleotides and 5000 nucleotides in length.

54. A mammalian cell comprising a polynucleotide according to claim 1, wherein said polynucleotide is stably integrated into a chromosome of said cell.

55. A mammalian cell of claim 54, wherein said cell comprises an AAV rep gene and an AAV cap gene.

56. A mammalian cell of claim 54, wherein said cell comprises an AAV rep gene and an AAV cap gene stably integrated into a chromosome of said cell.

57. A mammalian cell comprising a polynucleotide according to claim 17, wherein said polynucleotide is stably integrated into a chromosome of said cell.

58. A mammalian cell of claim 57, wherein said cell comprises an AAV rep gene and an AAV cap gene.

59. A mammalian cell of claim 57, wherein said cell comprises an AAV rep gene and an AAV cap gene stably integrated into a chromosome of said cell.

60. A mammalian cell comprising a polynucleotide according to claim 23, wherein said polynucleotide is stably integrated into a chromosome of said cell.

61. A mammalian cell of claim 60, wherein said cell comprises an AAV rep gene and an AAV cap gene.

62. A mammalian cell of claim 60, wherein said cell comprises an AAV rep gene and an AAV cap gene stably integrated into a chromosome of said cell.

63. A polynucleotide according to claim 1 wherein the region containing the ITR and the one or more transcriptionally active elements comprises a heterologous transcription initiator sequence.

64. A polynucleotide according to claim 1 wherein the region containing the ITR and the one or more transcriptionally active elements comprises a TATA box as a transcription initiator sequence.

65. A polynucleotide according to claim 17 wherein the region containing the ITR and the one or more transcriptionally active elements comprises a heterologous transcription initiator sequence.

66. A polynucleotide according to claim 17 wherein the region containing the ITR and the one or more transcriptionally active elements comprises a TATA box as a transcription initiator sequence.

67. A polynucleotide according to claim 23 wherein the region containing the ITR and the one or more transcriptionally active elements comprises a heterologous transcription initiator sequence.

68. A polynucleotide according to claim 23 wherein the region containing the ITR and the one or more transcriptionally active elements comprises a TATA box as a transcription initiator sequence.

69. A plasmid comprising a polynucleotide of claim 1, further comprising an element selected from the group consisting of an origin of replication and a reporter gene.

70. A plasmid comprising a polynucleotide of claim 17, further comprising an element selected from the group consisting of an origin of replication and a reporter gene.

71. A plasmid comprising a polynucleotide of claim 23, further comprising an element selected from the group consisting of an origin of replication and a reporter gene.

72. An AAV viral particle comprising a polynucleotide of claim 1.

73. An AAV viral particle according to claim 72, wherein the polynucleotide is between 4600 nucleotides and 5000 nucleotides in length.

74. An AAV viral particle comprising a polynucleotide of claim 17.

75. An AAV viral particle according to claim 74, wherein the polynucleotide is between 4600 nucleotides and 5000 nucleotides in length.

76. An AAV viral particle comprising a polynucleotide of claim 23.

77. An AAV viral particle according to claim 76, wherein the polynucleotide is between 4600 nucleotides and 5000 nucleotides in length.

78. A mammalian cell comprising a polynucleotide according to claim 29, wherein said polynucleotide is stably integrated into a chromosome of said cell.

79. A mammalian cell of claim 78, wherein said cell comprises an AAV rep gene and an AAV cap gene.

80. A mammalian cell of claim 78, wherein said cell comprises an AAV rep gene and an AAV cap gene stably integrated into a chromosome of said cell.

81. A mammalian cell comprising a polynucleotide according to claim 36, wherein said polynucleotide is stably integrated into a chromosome of said cell.

82. A mammalian cell of claim 81, wherein said cell comprises an AAV rep gene and an AAV cap gene.

83. A mammalian cell of claim 81, wherein said cell comprises an AAV rep gene and an AAV cap gene stably integrated into a chromosome of said cell.

84. A mammalian cell comprising a polynucleotide according to claim 45, wherein said polynucleotide is stably integrated into a chromosome of said cell.

85. A mammalian cell of claim 84, wherein said cell comprises an AAV rep gene and an AAV cap gene.

86. A mammalian cell of claim 84, wherein said cell comprises an AAV rep gene and an AAV cap gene stably integrated into a chromosome of said cell.

87. A polynucleotide according to claim 17 wherein the transcriptional activity is increased at least about 7-fold relative to a polynucleotide containing the ITR and lacking the one or more transcriptionally active elements under conditions permissive for transcription.

88. A polynucleotide according to claim 17 wherein the transcriptional activity is increased at least about 10-fold relative to a polynucleotide containing the ITR and lacking the one or more transcriptionally active elements under conditions permissive for transcription.

89. A polynucleotide according to claim 17 wherein the transcriptional activity is increased at least about 40-fold relative to a polynucleotide containing the ITR and lacking the one or more transcriptionally active elements under conditions permissive for transcription.

90. A polynucleotide according to claim 17 wherein the transcriptional activity is increased at least about 50-fold relative to a polynucleotide containing the ITR and lacking the one or more transcriptionally active elements under conditions permissive for transcription.

91. A polynucleotide according to claim 23 wherein the transcriptional activity is increased at least about 7-fold relative to a polynucleotide containing the ITR and lacking the one or more transcriptionally active elements under conditions permissive for transcription.

92. A polynucleotide according to claim 23 wherein the transcriptional activity is increased at least about 10-fold relative to a polynucleotide containing the ITR and lacking the one or more transcriptionally active elements under conditions permissive for transcription.

93. A polynucleotide according to claim 23 wherein the transcriptional activity is increased at least about 40-fold relative to a polynucleotide containing the ITR and lacking the one or more transcriptionally active elements under conditions permissive for transcription.

94. A polynucleotide according to claim 23 wherein the transcriptional activity is increased at least about 50-fold relative to a polynucleotide containing the ITR and lacking the one or more transcriptionally active elements under conditions permissive for transcription.

95. A polynucleotide according to claim 29 wherein the second AAV ITR is a wild-type ITR.

96. A polynucleotide according to claim 29 wherein the second AAV ITR is a transcriptionally-activated ITR.

97. A polynucleotide according to claim 29 wherein the second AAV ITR is a D sequence.

98. A polynucleotide according to claim 29 wherein the second AAV ITR is a trs.

99. A polynucleotide according to claim 29 wherein the second AAV ITR is a portion of a wild-type ITR.

100. A polynucleotide according to claim 36 wherein the second AAV ITR is a wild-type ITR.

101. A polynucleotide according to claim 36 wherein the second AAV ITR is a transcriptionally-activated ITR.

102. A polynucleotide according to claim 36 wherein the second AAV ITR is a D sequence.

103. A polynucleotide according to claim 36 wherein the second AAV ITR is a trs.

104. A polynucleotide according to claim 36 wherein the second AAV ITR is a portion of a wild-type ITR.

105. A polynucleotide according to claim 45 wherein the second AAV ITR is a wild-type ITR.

106. A polynucleotide according to claim 45 wherein the second AAV ITR is a transcriptionally-activated ITR.

107. A polynucleotide according to claim 45 wherein the second AAV ITR is a D sequence.

108. A polynucleotide according to claim 45 wherein the second AAV ITR is a trs.

109. A polynucleotide according to claim 45 wherein the second AAV ITR is a portion of a wild-type ITR.

* * * * *